United States Patent
Muehlberg et al.

(10) Patent No.: US 12,299,075 B2
(45) Date of Patent: May 13, 2025

(54) COMPUTER-IMPLEMENTED METHOD FOR PARAMETRIZING A FUNCTION FOR EVALUATING A MEDICAL IMAGE DATASET

(71) Applicant: Siemens Healthcare GmbH, Erlangen (DE)

(72) Inventors: Alexander Muehlberg, Nuremberg (DE); Oliver Taubmann, Weilersbach (DE); Alexander Katzmann, Fuerth (DE); Felix Denzinger, Nuremberg (DE); Felix Lades, Erlangen (DE); Rainer Kaergel, Stegaurach (DE); Felix Durlak, Langenzenn (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 672 days.

(21) Appl. No.: 17/382,588

(22) Filed: Jul. 22, 2021

(65) Prior Publication Data

US 2022/0036136 A1 Feb. 3, 2022

(30) Foreign Application Priority Data

Jul. 28, 2020 (EP) .................................... 20188174

(51) Int. Cl.
*G06F 18/21* (2023.01)
*G06F 18/214* (2023.01)
(Continued)

(52) U.S. Cl.
CPC .......... *G06F 18/217* (2023.01); *G06F 18/214* (2023.01); *G06F 18/24765* (2023.01);
(Continued)

(58) Field of Classification Search
CPC ................. G06F 18/217; G06F 18/214; G06F 18/24765; G06N 3/045; G06N 3/08;
(Continued)

(56) References Cited

U.S. PATENT DOCUMENTS

| 7,995,810 B2 * | 8/2011 | Li | G06T 7/12 |
| | | | 382/128 |
| 10,032,281 B1 * | 7/2018 | Ghesu | G16H 50/70 |

(Continued)

FOREIGN PATENT DOCUMENTS

CN 110889005 A 3/2020

OTHER PUBLICATIONS

"Request for further processing" application EP20188174 dated Oct. 7, 2022 (Year: 2022).*

(Continued)

*Primary Examiner* — Juan A Torres
(74) *Attorney, Agent, or Firm* — Harness, Dickey & Pierce, P.L.C.

(57) ABSTRACT

A computer-implemented method and system are for parametrizing a function including a processing algorithm and a representation generator, the representation generator being designed to generate at least one representation. In an embodiment, the method includes using an optimization algorithm to determine the processing algorithm and the at least one representation parametrization. The optimization algorithm optimizes a measure for the performance of the processing algorithm when operating on a set of training representations generated by applying the representation generator to training medical image datasets, by varying on the one hand the content of the at least one representation parametrization and/or the number of used representation parametrizations and on the other hand the processing algorithm and the algorithm parameters.

20 Claims, 8 Drawing Sheets

(51) Int. Cl.
  *G06F 18/24* (2023.01)
  *G06N 3/045* (2023.01)
  *G06V 10/25* (2022.01)
  *G16H 30/40* (2018.01)

(52) U.S. Cl.
  CPC .............. *G06N 3/045* (2023.01); *G06V 10/25* (2022.01); *G16H 30/40* (2018.01); *G06V 2201/03* (2022.01)

(58) Field of Classification Search
  CPC ........ G06N 3/084; G06N 20/00; G06V 10/25; G06V 2201/03; G16H 30/40; G06T 7/0012; G06T 2207/20081; G06T 2207/20084; G06T 2207/30048; G06T 2207/30061; G06T 2207/30096
  USPC ........................................................ 382/128
  See application file for complete search history.

(56) References Cited

U.S. PATENT DOCUMENTS

| | | | |
|---|---|---|---|
| 10,825,168 B2* | 11/2020 | Tegzes | G06T 7/11 |
| 2008/0118131 A1 | 5/2008 | Skinner et al. | |
| 2018/0144214 A1 | 5/2018 | Hsieh et al. | |
| 2018/0315188 A1* | 11/2018 | Tegzes | G06T 7/11 |
| 2019/0365341 A1 | 12/2019 | Chan et al. | |
| 2020/0058390 A1 | 2/2020 | Kohle et al. | |
| 2020/0272864 A1* | 8/2020 | Faust | G06V 10/764 |
| 2021/0272275 A1* | 9/2021 | S | G16H 30/40 |
| 2021/0272277 A1* | 9/2021 | Ogino | A61B 6/032 |

OTHER PUBLICATIONS

Ghesu, "Marginal Space Deep Learning: Efficient Architecture for Volumetric Image Parsing" IEEE Transactions on Medical Imaging Year: 2016 | vol. 35, Issue: 5. (Year: 2016).*
Amended claims filed after receipt of (European) search report for application EP20188174 dated Oct. 7, 2022. (Year: 2022).*
Annex to communication from Examining Division for application EP20188174 dated Feb. 8, 2024. (Year: 2024).*
Adnan Qayyum, "Medical Image Retrieval using Deep Convolutional Neural Network". Mar. 24, 2017 (Year: 2017).*
Denzinger, Felix et al: "Deep Learning Algorithms for Coronary Artery Plaque Characterisation from CCTA Scans", 2019.
Litjens, Geert et al. "A Survey on Deep Learning in Medical Image Analysis" Medical Image Analysis, vol. 42, pp. 60-88, 2017, XP080747655, Issn: 1361-8415, Doi: 10.1016/J.MEDIA.2017.07.005.
Pham, H. et. al., "Efficient Neural Architecture Search via Parameter Sharing", International conference on machine learning, arXiv:1802.03268, 2018.
Kazi, Anees et al.; "Automatie Classification of Proximal Femur Fractures Based on Attention Models", Sep. 7, 2017 (Sep. 7, 2017), Big Data Analytics in the Social and Ubiquitous Context : 5TH International Workshop on Modeling Social Media, Msm 2014, 5TH International Workshop on Mining Ubiquitous and Social Environments, Muse 2014 and First International Workshop on Machine Le, XP047437130, Isbn: 978-3-642-17318-9 [retrieved on Sep. 7, 2017].
Elsken, T. et al., "Neural Architecture Search: A Survey", Journal of Machine Learning Research 20 (2019), pp. 1-21, 2019.
European Search Report for European Application No. 20188174.5 dated Feb. 25, 2021.

* cited by examiner

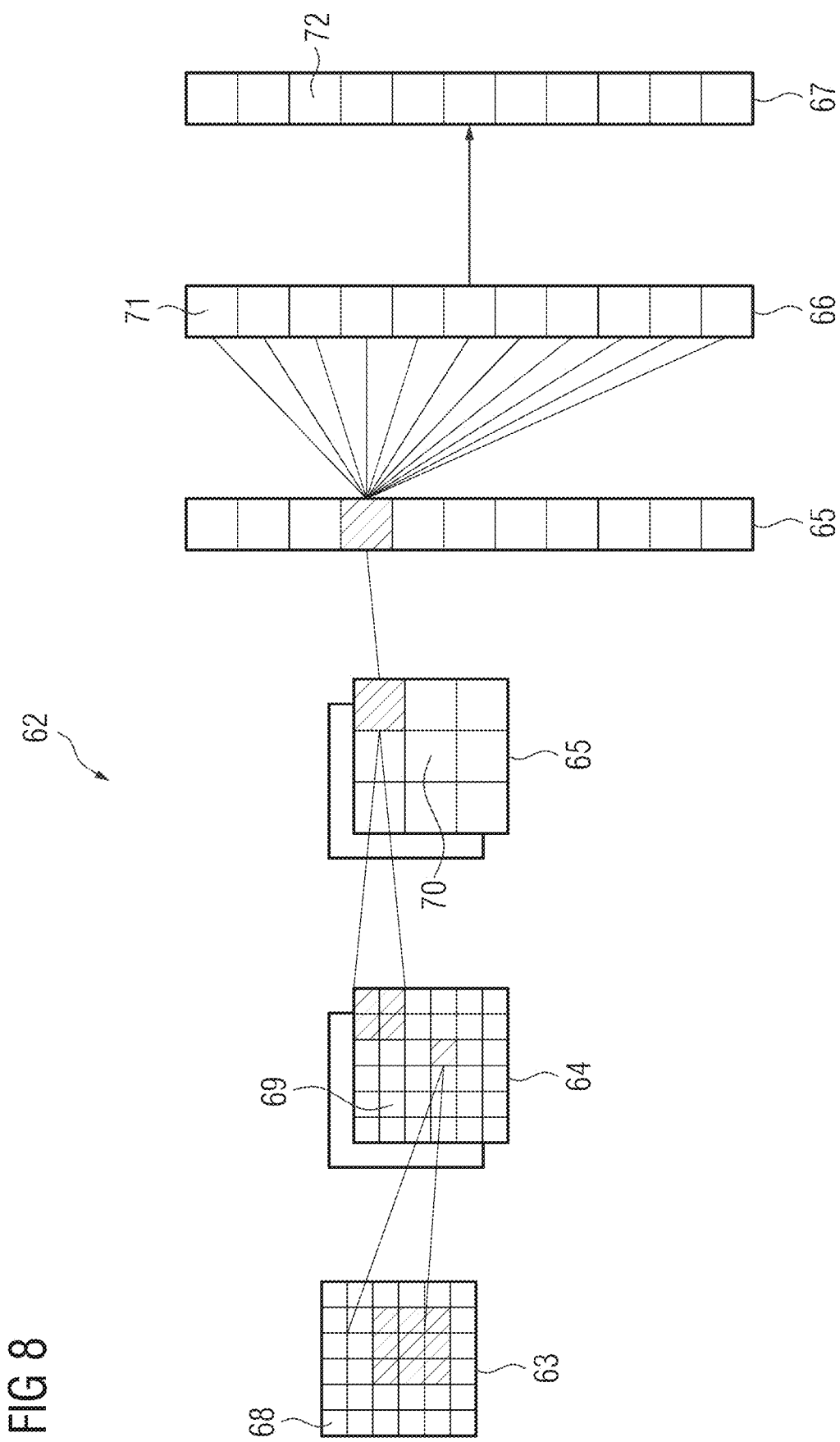

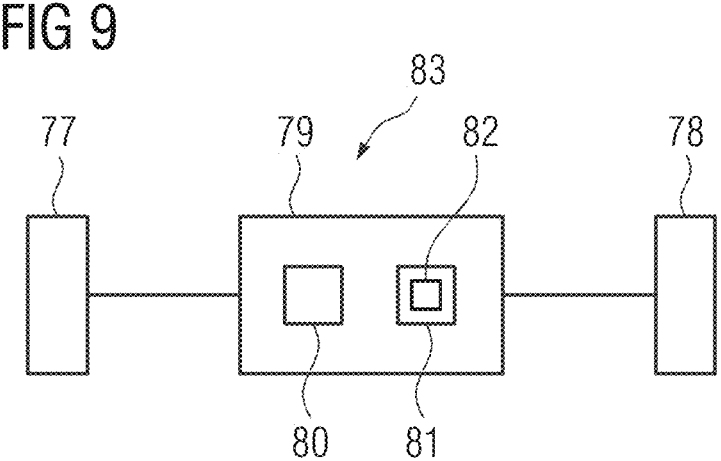

COMPUTER-IMPLEMENTED METHOD FOR PARAMETRIZING A FUNCTION FOR EVALUATING A MEDICAL IMAGE DATASET

PRIORITY STATEMENT

The present application hereby claims priority under 35 U.S.C. § 119 to European patent application number EP 20188174 filed Jul. 28, 2020, the entire contents of which are hereby incorporated herein by reference.

FIELD

Example embodiments of the invention generally relate to a computer-implemented method for parametrizing a function for evaluating a medical image dataset concerning a region of interest; a computer-implemented method for evaluating medical image data; a providing system; a computer program and a computer-readable medium.

BACKGROUND

Deep learning techniques are promising candidates for automating tasks in medical image analysis. By using supervised learning and a sufficiently large training dataset many tasks, that would normally require manual image analysis by trained medical personnel, can be automated or at least supported by deep learning techniques. A multitude of tasks that can be solved by deep learning techniques are described in the paper G. Litjens et al., "A Survey on Deep Learning in Medical Image Analysis", Medical image analysis, 42 (2017), S. 60.

A major challenge in using deep learning techniques is the design of a suitable neural architecture, e.g. an architecture of a neural network or more specifically a convolutional neural network that is well suited to the task at hand. While using a strongly connected architecture and an essentially free parametrization of e.g. input weights, etc. can be advantageous for some tasks, it is often also advantageous to limit the number of free parameters learned during the learning process to avoid the necessity of excessively large training datasets and long learning times.

Since handcrafting of a neural architecture is laborious, requires long testing times and is often based on trial and error, approaches for automated systems for determining neural architectures were a highly active topic in recent years. An overview of relevant techniques is given in the article T. Elsen et al., "Neural Architecture Search: A Survey", Journal of Machine Learning Research 20 (2019), S. 1 the entire contents of which are hereby incorporated herein by reference. As far as neural architecture searches are discussed in the following text, examples will focus on one-shot architecture searches, especially the efficient neural architecture search (ENAS) discussed in the article H. Pham et al., "Efficient Neural Architecture Search via Parameter Sharing", International conference on machine learning, 2018 the entire contents of which are hereby incorporated herein by reference.

A remaining problem of deep learning architectures, especially when combined with automated neural architecture searches, is the reliance on high-dimensional input data, e.g. three-dimensional medical image datasets recorded in relatively high resolution by computed tomography, magnetic resonance tomography or similar medical imaging approaches. Increasing the amount of data in the individual dataset to be analyzed increases the complexity of the necessary neural architecture and therefore the necessary time to find a good network architecture, to reach conversions during training and the amount of training data necessary. Even hundreds or thousands of representative cases can often not be sufficient to reach a good performance of the trained algorithm.

While this problem has been tracked with various techniques like data augmentation, e.g. by using generative adversarial networks, and/or regularization, e.g. by batch normalization, autoencoders, etc., currently no generally applicable approach is available. This is especially problematic, since these advanced techniques are often not directly usable by medical researchers and often need considerable experience in deep learning architectures and methods to actually improve the results.

The recent paper F. Denzinger et al., "Deep Learning Algorithms for Coronary Artery Plaque Characterization from CCTA Scans", Bildverarbeitung für die Medizin 2020, the entire contents of which are hereby incorporated herein by reference, discusses the extraction of two orthogonal views of a lesion of interest and the use of these two 2D-views as input for a neural network. It was found that this approach slightly outperforms approaches based on three-dimensional input data and allows for a faster training. This example indicates that the selection of a suitable data representation for the problem under investigation can noticeably improve the training and performance of deep learning architectures, especially when the available training data is limited. The selection of the used data representation is however purely based on intuition. Typically, little thought is put into selecting a suitable data representation and there is no systematic selection process.

It is however typically not possible for an architect of deep learning applications to reliably predict if a certain data representation will be well-suited or less well-suited for determining certain features by an algorithm trained by deep learning. Therefore, types of input data that are expected to be reasonably well-suited to any kind of problem are typically used as input data for deep learning architectures, e.g. a relatively large amount of equally spaced slices, multiple 3D-volumes, etc. While this approach typically allows for robust convergence of the learning process when a sufficient amount training data is available, this approach typically leads to unnecessarily complex algorithms and increases the amount of necessary training data and processing time required for training and for applying the trained algorithm.

SUMMARY

At least one embodiment of the present invention provides an improved approach to machine learning that especially allows for a training using less time and/or requiring less training data.

In at least one embodiment, a computer-implemented method is for parametrizing a function for evaluating a medical image dataset concerning a region of interest, wherein the function comprises a processing algorithm determined by the parametrization of the function and a representation generator, wherein the representation generator is designed to generate at least one representation of the region of interest based on the medical image dataset and a respective representation parametrization determined by the parametrization of the function and wherein the processing algorithm is designed to determine at least one output parameter based on the at least one representation and multiple algorithm parameters, the method comprising the steps:

receiving a training dataset comprising multiple training medical image datasets, receiving representation information, using an optimization algorithm to determine the processing algorithm and the at least one representation parametrization, wherein the optimization algorithm optimizes a measure for the performance of the processing algorithm when the processing algorithm is operating on a set of training representations generated by applying the representation generator to at least a subset of the training medical image datasets using the at least one representation parametrization by varying on the one hand the content of the at least one representation parametrization based on the representation information and/or the number of used representation parametrizations and on the other hand the processing algorithm within a given search space and the algorithm parameters, providing the at least one determined representation parametrization and the determined processing algorithm or processing parameters describing the determined processing algorithm to parametrize the function.

At least one embodiment of the invention also concerns a method for evaluating medical image data, comprising the steps:

receiving a medical image dataset concerning a region of interest as input data, applying a function trained by a machine learning algorithm to the medical image dataset to determine at least one output parameter, wherein the function comprises a processing algorithm determined and/or parametrized by machine learning and a representation generator, wherein the representation generator generates at least one representation of the region of interest based on the medical image dataset and a respective representation parametrization determined by machine learning, and wherein the processing algorithm determines the output parameter based on the at least one representation, providing the output parameter as output data.

Additionally, at least one embodiment of the invention concerns a providing system comprising a first interface, configured for receiving input data, a second interface, configured for providing output data, a computation unit, configured to determine the at least one determined representation parametrization and the determined processing algorithm or parameters describing the determined processing algorithm as the output data based on the training dataset and the representation information as input data according to the computer-implemented method for parametrizing a function, and/or to determine the output parameter as output data based on the medical image dataset as input data according to the computer-implemented method for evaluating medical image data.

A computer program according to at least one embodiment of the present invention comprises instructions which, when the computer program is executed by a computer, causes the computer to carry out the computer-implemented method for parameterizing a function according to at least one embodiment of the present invention and/or the computer-implemented method for evaluating medical image data according to at least one embodiment of the present invention.

A computer-readable medium according to at least one embodiment of the present invention comprises a computer program according to at least one embodiment of the present invention.

Additionally, at least one embodiment of the invention concerns a computer-implemented method for parametrizing a function for evaluating a medical image dataset concerning a region of interest, the function including a processing algorithm determined by the parametrization of the function and a representation generator, the representation generator being designed to generate at least one representation of the region of interest based on the medical image dataset and a respective representation parametrization determined by the parametrization of the function, and the processing algorithm being designed to determine at least one output parameter based on the at least one representation and multiple algorithm parameters, the computer-implemented method comprising:

receiving a training dataset including multiple training medical image datasets;

receiving representation information;

determining, using an optimization algorithm, the processing algorithm and the at least one representation parametrization, the optimization algorithm optimizing a measure for performance of the processing algorithm when the processing algorithm is operating on a set of training representations generated by applying the representation generator to at least a subset of the training medical image datasets using the at least one representation parametrization by varying on the one hand the content of the at least one representation parametrization based on at least one of the representation information and a number of used representation parametrizations, the processing algorithm being within a search space and the algorithm parameters; and providing the at least one representation parametrization determined and providing the processing algorithm determined or processing parameters describing the processing algorithm determined, to parametrize the function.

Additionally, at least one embodiment of the invention concerns a computer-implemented method for evaluating medical image data, comprising:

receiving a medical image dataset concerning a region of interest as input data;

applying a function trained by a machine learning algorithm to the medical image dataset to determine at least one output parameter, the function including a processing algorithm at least one of determined and parametrized by machine learning and a representation generator, the representation generator generating at least one representation of a region of interest based on the medical image dataset and a respective representation parametrization determined by machine learning, and the processing algorithm determining the at least one output parameter based on the at least one representation; and providing the at least one output parameter as output data.

Additionally, at least one embodiment of the invention concerns a providing system, comprising:

a first interface, configured to receive input data;

a second interface, configured to provide output data; and at least one processor, configured to at least one of receive a training dataset including multiple training medical image datasets, receive representation information, determine, using an optimization algorithm, the processing algorithm and the at least one representation parametrization, the optimization algorithm optimizing a measure for performance of the processing algorithm when the processing algorithm is operating on a set of training representations generated by applying the representation generator to at least a subset of the training medical image datasets using the at least one representation parametrization by varying on the one hand the content of the at least one representation parametrization based on at least one of the representation information and a number of used representation parametrizations, the processing algorithm being within a search space and the algorithm parameters, and provide the at least one representation parametrization determined and providing the processing algorithm determined or processing parameters describing the processing algorithm determined, to parametrize the function; and receive a medical image dataset concerning a region of interest as input data, apply a function trained by a machine learning algorithm to the medical image dataset to determine at least one output parameter, the function including a processing algorithm at least one of determined and parametrized by machine learning and a representation generator, the representation generator generating at least one representation of a region of interest based on the medical image dataset and a respective representation parametrization determined by machine learning, and the processing algorithm determining the at least one output parameter based on the at least one representation, and providing the at least one output parameter as output data.

Additionally, at least one embodiment of the invention concerns a non-transitory computer program storing instructions which, when the computer program is executed by a computer, cause the computer to carry out the computer-implemented method of claim an embodiment.

Additionally, at least one embodiment of the invention concerns a non-transitory computer-readable medium storing a computer program including instructions which, when the computer program is executed by a computer, cause the computer to carry out the computer-implemented method of an embodiment.

BRIEF DESCRIPTION OF THE DRAWINGS

Other objects and features of embodiments of the present invention will become apparent from the following detailed description considered in conjunction with the accompanying drawings. The drawings, however, are only principle sketches designed solely for the purpose of illustration and do not limit the invention. The drawings show schematically.

DETAILED DESCRIPTION OF THE EXAMPLE EMBODIMENTS

Figure 1:
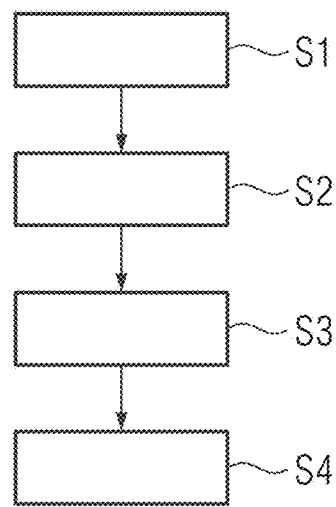
FIG. 1 a flowchart of an example embodiment of a computer-implemented method for evaluating medical image data according to the present invention, FIG. 2 the interaction of relevant algorithms and data structures in an example embodiment of the computer-implemented method for evaluating medical image data according to the present invention, FIG. 3 a flowchart of an example embodiment of a computer-implemented method for parameterizing a function for evaluating a medical image dataset according to the present invention, FIG. 4 relevant algorithms and data structure of an embodiment of such a method, FIG. 5 an example of possible representations of a medical image dataset concerning a vessel as the region of interest generated by a representation generator, FIG. 6 a schematic representation of the search space for a processing algorithm, FIG. 7 a simple example of a neural network, FIG. 8 a simple example of a convolutional neural network, and FIG. 9 an example embodiment of a providing system according to the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, a computer-implemented method is for parametrizing a function for evaluating a medical image dataset concerning a region of interest, wherein the function comprises a processing algorithm determined by the parametrization of the function and a representation generator, wherein the representation generator is designed to generate at least one representation of the region of interest based on the medical image dataset and a respective representation parametrization determined by the parametrization of the function and wherein the processing algorithm is designed to determine at least one output parameter based on the at least one representation and multiple algorithm parameters, the method comprising the steps:

receiving a training dataset comprising multiple training medical image datasets, receiving representation information, using an optimization algorithm to determine the processing algorithm and the at least one representation parametrization, wherein the optimization algorithm optimizes a measure for the performance of the processing algorithm when the processing algorithm is operating on a set of training representations generated by applying the representation generator to at least a subset of the training medical image datasets using the at least one representation parametrization by varying on the one hand the content of the at least one representation parametrization based on the representation information and/or the number of used representation parametrizations and on the other hand the processing algorithm within a given search space and the algorithm parameters, providing the at least one determined representation parametrization and the determined processing algorithm or processing parameters describing the determined processing algorithm to parametrize the function.

Common approaches to machine learning use a fixed type of input data, e.g. the complete medical image dataset or a predefined representation of the region of interest shown in the medical image dataset, e.g. a certain slice or projection image. At least one embodiment of the inventive method allows for a variation of the used representation or even the number of used representations within the optimization algorithm. It can therefore e.g. reduce the amount of input data and therefore the network complexity by discarding certain representations that do not or hardly improve the result. Additionally or alternatively, it can e.g. slightly vary representations, e.g. the selected layer, a projection direction, etc., to further improve the result.

As an example, a user can generate representations during a manual data analysis. E.g. a radiologist can generate multiple, e.g. 3 to 5, representations for a given medical image dataset. He or she can use a toolkit to generate these representations during his or her normal workflow and just indicate any representations generated that are relevant for a given diagnostic task according to his or her medical or radiological intuition. E.g. an overview projection and a few selected layers of a 3D-Dataset can be selected.

A representation parametrization used in the toolkit can then be used to generate these representations for all medical image datasets used in a study. To allow for such a transfer it is advantageous to use an anatomical coordinate system to define positions and orientations. These representations or the representation parametrization describing these representations can then be used as the representation information. The optimization algorithm can then be used to simultaneously optimize the representations used as input data and the used processing algorithm, e.g. by using a neural architecture search.

In a first part of the optimization, the most relevant subset of the suggested representations can automatically be selected by the optimization algorithm. It can e.g. be determined during the optimization, that one or multiple representations suggested by the radiologist seem to have little to no relevance. By reducing the number of used representations, the complexity of the processing algorithm can be reduced and therefore less training data is required to provide a highly performant algorithm.

Optionally a second part of the optimization algorithm can then be used to slightly vary the representations, e.g. by slightly modifying projection directions, layer selections, etc. to further improve the measure of performance. Feedback can be provided to the radiologist, e.g. informing him or her, that certain representations where found to have little to no relevance or by indication especially relevant regions of representations, e.g. by providing saliency maps of the processing algorithm.

Once a good selection of representations and therefore of representation parametrizations parametrizing the representation generator is found, the representation parametrization can then be shared with other medical practitioners, used to further train the selected processing algorithm by generating additional representations, etc. Various steps of the example workflow discussed above will be discussed in more detail later. While only the intuition of a single user is taken into account in the previous example, representation parametrizations concerning representations considered to be relevant by different users can be merged to provide the representation information.

It was found that purely varying the input data of the processing algorithm and the algorithm parameters, e.g. input weights of the artificial neurons, that can also be called nodes, or convolution kernels, does typically not achieve optimal performance, since a certain neural architecture might be well-suited for a certain set of representations but not suited for a different set of representations that might actually be better suited for the problem at hand. At least one embodiment of the inventive method therefore uses a combined optimization algorithm, that also varies the processing algorithm within the search space and therefore allows for a matching of the used neural architecture to the used representation or representations.

Since at least one embodiment of the inventive method therefore allows for the selection of a well-suited representation or set of representations as the input data, the complexity of the processing algorithm itself, that can e.g. be implemented as a neural network, can be noticeably reduced. In many cases a performant solution can only be found due to this reduction in complexity, especially when only a limited amount of training data is available. Performant solutions can often only be found by a simultaneous or iterative optimization of the used representations and the used optimization algorithm, since the optimum solution will often use a non-trivial combination of the right data representation and the right algorithm structure. The reduction in complexity also results in several further advantages. The performance of the trained algorithm can improve. Additionally, a faster convergence of the training process can be achieved and less training data is necessary for the training.

At least one embodiment of the inventive method can be used to parametrize a function for a multitude of purposes and therefore a multitude of possible output parameters. The output parameters can be relatively low-level parameters, e.g. a classification of tissue, organs, etc., an automated segmentation or a registration of an image volume described by the medical image dataset to a predefined coordinate system. It was however found that the discussed approach is especially suitable for the determination of higher-level output parameters that can e.g. support medical personnel in forming a diagnosis and/or in cases that process medical image datasets with a high dimensionality, e.g. when processing three-dimensional image data concerning a lung or an artery tree. Using e.g. a neural network to process these types of datasets can be challenging. By e.g. using a selected number of representations instead of the full dataset the complexity of the input data can be reduced. This can massively simplify the application of machine learning to such problems.

The parametrized function can e.g. be applied to medical image datasets depicting lung parenchyma to support clinical decisions concerning malignancies like chronic obstructive pulmonary disease or interstitial lung disease. Using the whole three-dimensional lung region as a direct input to the processing algorithm is highly problematic, since it results in a large memory requirement, reducing possible batch sizes, and leads to processing of image data that is in large parts irrelevant and thus unnecessarily, increasing the complexity of the processing algorithm.

The previously discussed method can therefore be used to learn, which representations are actually relevant for supporting a diagnosis concerning a certain lung disease. For chronic obstruction pulmonary disease and other diseases correlating with emphysema it might e.g. be sufficient to use a simple 2D overview image that depicts the geometric distribution of the emphysema. Other pulmonary diseases correlate with inflammatory processes of the airways that manifest as a thickening of their walls and might be well visualized in stacks of multiplanar reformatted representations orthogonal to the airway direction and/or curved planar representations that immediately illustrate the wall thickness of an airway along the different generations or even more condensed as multi-path curved planar representation. It would also be possible to use unfolded views of multiple airways at once.

Similar visualizations might also capture information on diseases like bronchiectasis, where the complete bronchovascular bundle is relevant to detect abnormal airway lumen diameters in relation to the corresponding pulmonary artery, leading to novel co-curved planar representation and co-unfoldings of airway and artery.

By selecting multiplanar reformatted representation depicting regions of interest with signs like centrilobular micronodules related to respiratory bronchiolitis ILD, the system could learn to predominantly sample from certain, in this case distal, areas of the lung in relation to the airway tree and automatically find a rotation angle that shows the full extent of important clinical signs like tree-in-bud.

As discussed below, the representation information can depend on user input defining relevant representations. Meaningful sample positions could therefore also be automatically identified, if the user selects visualizations of positions that are only identifiable if diseased, e.g. lobular boundaries that become visible in the presence of air trapping.

It is obvious from the previous discussion, that in principle a huge number of representations is possible. The representation generator can provide a tool kit to generate all of these representations. Since a brute force sampling of the full range of possible representations would lead to prohibitively long training times, the received representation information can be used to limit the search space for the representation parametrizations and therefore for the possible representation and/or to provide one or multiple representation parametrizations as starting points for the optimization as discussed in more detail below.

The representation information might be information describing what representations are considered to be relevant for the determination of certain output parameters by an expert or a group of experts.

A second example application concerns the field of cardiology. The initially discussed publication by Denzinger et al., the entire contents of which are hereby incorporated herein by reference, already compares the performance of deep learning algorithms using various different representations as input data. This publication suggests to reshape a lesion of interest into a multi-planar reformatted image stack created by interpolating planes orthogonal to each centerline point of the vessel. This image stack is then used to generate different predetermined sets of representations that are then processed by a neural network with a fixed architecture. One set of representations comprises orthogonal slices along the centerline. The performance using this set was compared to the performance using a series of cubes along the image stack as representations and the use of mean and maximum intensity projection images as representations.

Therefore, in the discussed publication only a very limited number for representations and only one parametrization of each representation was tested. The publication also uses a fixed neural architecture. At least one embodiment of the inventive method could therefore further improve the performance, e.g. by varying the position and/or orientation of slices and/or projections and/or the spacing and/or the sizes of selected cubes, by combining multiple different types of representations as input, etc. Since the architecture of the processing algorithm can be varied simultaneously during the optimization, an optimum performance can be achieved for the optimum set of representations used as input data.

The algorithm parameters can be all parameters determined during a normal machine learning when training a processing algorithm with a given neural architecture, e.g. input weights of the individual nodes or parameters of the respective filter kernel in a convolutional neural network. The algorithm parameters can already be determined during the optimization algorithm. It is e.g. possible to perform a complete training of the given processing algorithm for a given representation parametrization or set of representation parametrizations to determine the measure for the performance of the processing algorithm.

While such a complete training might be rather computation intensive, it might still be possible, e.g. when parameter sharing between different architectures is used. An example of parameter sharing are one-shot architecture searches, as e.g. used in ENAS. Many performance estimation strategies do however use smaller training datasets, a learning curve extrapolation or other approaches to reduce the amount of calculations necessary for the performance estimation. These approaches are e.g. discussed in the paper by T. Elsken et al. that was already cited. Typically, these approaches will not perform a complete training of the determined architecture.

It can therefore be advantageous to determine the algorithm parameters in a further step by using the further optimization algorithm that can be any algorithm usable to train the processing algorithm by machine learning. It is e.g. possible to use supervised learning with training data comprising desired output values.

In general, the algorithm parameters can be adapted by means of training, in particular supervised training, semi-supervised training unsupervised training, reinforcement learning and/or active learning. Furthermore, representation learning can be used. In particular, the algorithm parameters can be adapted iteratively by several steps of training. The processing algorithm can comprise a neural network, a support vector machine, a decision tree and/or a Bayesian network and/or the processing algorithm can be based on k-means clustering, Q-learning, genetic algorithms and/or association rules. In particular, a neural network can be a deep neural network, a convolutional neural network or a deep convolutional neural network. Furthermore, a neural network can be an adversarial network, a deep adversarial network and/or a generative adversarial network.

The previously discussed approaches for training the processing algorithm, once it is determined by the optimization algorithm, can also be used within the optimization algorithm. Within the optimization algorithm the selection or determination of the used representation parametrization or representations and/or the processing algorithm can be based on Bayes optimization and/or evolutional algorithms.

The medical image dataset can be a three-dimensional image dataset, e.g. three-dimensional CT-, MRT-, or PET-data. Alternatively, the medical image dataset could e.g. be two-dimensional image data. The optimization algorithm could e.g. select a sub-set of possible representation parametrizations, e.g. 1-5 representation parametrizations, perform a neural architecture search based on representations determined using these representation parametrizations as training data, determining a performance for the found architecture, and iteratively repeat this process for different sub-sets of representation parametrizations. It is e.g. possible that the representation information defines a pool of possible representation parametrizations, e.g. 10 representation parametrizations, and the optimization algorithm chooses a sub-set of this pool. Once a relevant sub-set is found, the selected representation parametrization or parametrizations can be further modified within the optimization algorithm, e.g. by an evolutionary algorithm to further improve the measure of performance.

In the context of this document a sub-set is understood to comprise at least one element and preferably not all elements of a set or group. The representation parametrization can comprise only a single parameter, e.g. a type of the representation, a selected slice, a projection angle, etc. Preferably, it comprises multiple parameters, e.g. a used type of the representation and at least one parameter for this type.

The algorithm parameters can be determined by the optimization algorithm or by a further optimization algorithm, wherein the further optimization algorithm optimizes the measure or a further measure for the performance of the processing algorithm that was determined in the optimization algorithm when this processing algorithm is operating on the set or a further set of training representations generated by applying the representation generator to the training medical image datasets or to the sub-set or a further sub-set of the training medical image datasets using the at least one representation parametrization that was determined in the optimization algorithm by varying the algorithm parameters. As previously discussed, the algorithm parameters can be parameters typically determined during machine learning, e.g. parameters of a filter kernel of a convolutional neural network or input weights of individual nodes in an artificial neural network. They can therefore be determined with any known approach for machine learning that can be used as the further optimization algorithm. Alternatively, it would be possible to already perform a complete training of the processing algorithm during the optimization algorithm.

The search space can define multiple possible architectures for neural networks, wherein the selection of the processing algorithm in the optimization algorithm is the result of a neural architecture search, wherein free parameters of the neural network defined by the respective architecture, especially input weights of the nodes of the neural network, are defined by the algorithm parameters. The architecture of the respective processing algorithm can especially determine the output of which nodes depends on the output of which other nodes. E.g. the architecture can define if skip connections between nodes are present that allow for an input of data not only from nodes in an immediately previous layer of the network but from nodes of an earlier layer. Additionally or alternatively, the architecture can define if parallel processing branches are present, etc. The architecture can also define what type of operation is performed in a certain layer of a convolutional neural network and/or the activation functions of at least some of the nodes in the network. Therefore, the selection of the processing algorithm can determine the architecture of the network and the algorithm parameters can determine the parametrization of the neural network.

The search space can define multiple convolutional neural networks that differ with respect to the connections between layers and/or the type of operation performed by the respective layer. Alternatively, the search space can define multiple neural networks that differ with respect to the connections between nodes and/or the activation function used in at least one of the nodes. Examples for such search spaces are discussed in detail in the previously discussed papers by T. Elsken et al., and H. Pham et al, the entire contents of which are hereby incorporated herein by reference.

The size of the search space can be limited by posing certain limits on the architecture. It is e.g. already known, that a promising approach to designing neural networks, especially convolutional neural networks, is using repeated cells within the network that use the same architecture, but that can have a different parametrization and therefore different algorithm parameters applied. It is e.g. suggested by Pham et al. to only determine the architecture for a convolutional cell and for a reduction cell and then to use an alternating arrangement of these cells or an alternating arrangement of multiple copies of the convolutional cell and the reduction cell. Since only two different cells can be varied in this approach that comprise a limited number of convolutional layers or other nodes, the number of architectures in the search space can be limited, therefore allowing for a faster selection of the processing algorithm and a robust convergence of the selection process, even when using a relatively limited number of training medical image datasets.

The whole network formed by the stacking of these cells can then be trained and therefore the algorithm parameters for the full network can be determined. A further advantage of using repeating cells is the ability to use a limited algorithm, that can e.g. comprise a smaller number of such cells, to determine the measure for the performance of the processing algorithm and only train the complete processing algorithm once the architecture is determined.

As types of operation performed by the respective layer of a convolutional neural network, a maximum pooling, minimum pooling, average pooling, convolution, depth wise separable convolution or identity can be used. It is also possible to differentiate the type of operation according to the size of the used convolution kernel, e.g. to differentiate between a 3×3 convolution and a 5×5 convolution. Examples for types of activation functions that can be selected are tank, ReLU, identity and sigmoid.

The search space for the complete network or the repeated cells can especially be expressed as a graph with edges connecting individual nodes or layers of the network. The presence of a respective edge can indicate the dependence of the node or layer on a previous node or layer connected by this edge. An absence of an edge shows an independence of a certain node or layer from the output of the previous node or layer. Concerning the connections between the nodes or layers, the search space can therefore be parametrized by the presence or absence of the respective edge. Therefore, when the number of possible edges is described by N, the size of the search space concerning the connections can be given as 2N. The search space also comprises a selection of activation functions or operations performed by the respective node or layer. If the number of considered activation functions or operations is m and a number k of layers or nodes is considered, the search space for the activation functions or operations has a size of mk. The overall size of the search space can therefore be given as 2N*mk.

Splitting a complex network into several cells having the same architecture can therefore massively decrease the size of the search space and therefore reduce the amount of processing power and training data required to select the processing algorithm.

The representation parametrization can select between different types of representations, including at least two of: a projection image, especially an artificial x-ray image, a single slice of an image volume, a multi-planar reformatted representation, a curved planar reformation, an unfolded representation of a region of interest, a masked image, a representation generated using histogram equalization and/or a normalization. The individual mentioned types of representation are well-known in the prior art and are already used by medical personnel in evaluating medical image datasets. Masked images and representations based on histogram equalization and/or normalization, e.g. on a White Stripe normalization, can be based on the other types mentioned, e.g. on slices or projections, and the additional processing can e.g. be performed as post processing. In other words, the representation parametrization can determine, if masking and/or a histogram equalization and/or a normalization is performed or if none of these processing steps are performed.

Alternatively, the representation parametrization could only determine the further parametrization of a single type of representation, e.g. select between different projections, e.g. between an axial, sagittal, coronal and oblique projections. When the representation parametrization can select between different types of representations, the representation information can potentially limit the considered representations to a single type in some cases.

Using a representation parametrization that selects between different types of representation allows for at least one embodiment of the inventive method to choose from these different types of representations the one that leads to an optimum performance of the processing algorithm for the training medical image datasets or even to select combinations of different representations that might be advantageous for the determination of the at least one output parameter.

An unfolding of the region of interest might e.g. be relevant if the region of interest is an airway or an artery. It is also e.g. possible to co-unfold an airway and an artery. Mask images might be relevant when a contrast agent is used, e.g. for a background subtraction. A curved planar reformation might be relevant to display a vessel or an airway, but might also be used to e.g. depict the texture of a surface of a certain organ or a tumor. When multiple representation parametizations are selected to provide multiple representations as an input of the processing algorithm, those representation parametrizations can describe different representations or they can describe the same representation but differ with respect to further parameters, e.g. the selection of a used slice or a used plane. A further example of a useable representation would be a representation that is based on the Cinematic Rendering approach used in devices of the applicant to provide photo-realistic 3D-representations of CT- and MR-images.

A possible content of the representation parametrization can select a slice of an image volume defined by the medical image dataset as the representation, wherein the representation parametrization determines, which slice of the image volume is selected and/or the orientation of the slice. Additionally or alternatively, a possible content of the representation parametrization can select a projection image of the image volume as the representation, wherein the representation parametrization determines the direction of the projection. At least one embodiment of the inventive method can therefore e.g. select the slices and/or projections optimally suited to determine the output parameter or parameters. Similarly, further parameters of the other types of representations discussed above can be determined by the representation parametrization. As previously discussed, the optimum neural architecture for the chosen representation or set of representations can be selected by using a simultaneous optimization.

For a selection of slices or projections or a parametrization of the further mentioned types of representation, it can be advantageous to use an anatomical coordinate system. This can e.g. be realized by registering the image data of the respective medical image dataset to an atlas, by detecting certain landmarks in a medical image dataset and using the positions and/or distances between these landmarks to define an anatomical coordinate system etc. It is therefore e.g. possible to define an axial, coronal and segetal direction for projections and/or for a stacking direction of slices.

The representation information can comprise or define a set of predefined representation parametrizations, wherein the optimization algorithm selects one of or a sub-group of the predefined representation parametrizations in first alternative as the at least one determined representation parametrization or in a second alternative as at least one approximate representation parametrization, wherein the determination of the at least one representation parametrization in the second alternative is based on the at least one approximate representation parametrization.

The representation information can therefore in the first alternative define possible representation parametrizations. In this case, the purpose of the optimization algorithm is to select the representation parametrization or parametrizations defining the representation or combination of representations most suitable to determine the output parameter or parameters from the selection defined by the representation information.

In the second alternative, the optimization can be performed in two parts. The first part of the optimization selects the approximate representation parametrization or parametrizations that seems or seem to be the most promising starting point for a further search for the ideal representation parametrization or parametrizations. Once a promising candidate or multiple promising candidates are found, a variation of the approximate representation parametrization or parametrizations can be performed, e.g. by an evolutionary algorithm, to find representations that are even more suitable to determine the at least one output parameter.

The variation of the approximate representation parametrization can especially keep the type of representation used constant and only slightly vary the respective representation, e.g. by slightly varying an angle of a projection or the orientation and/or a position of a slice.

The method can comprise receiving user input by at least one user, wherein the predefined representation parametrizations are determined from that user input. The user input can especially be generated while a respective user is selecting or adjusting representations used during a manual evaluation of image data to determine the parameter or parameters to be determined by the function. In other words, the user input can define representations or the corresponding representation parametrizations that are considered to be relevant for a specific task, e.g. for forming a diagnosis or for discerning the presence of a certain feature in the medical image dataset.

It is especially advantageous, when the representation generator is already used by the user to define representations for manual inspection. In this case the respective representation parametrization used for this manual inspection can directly be used as part of the representation information. Alternatively, it is possible to provide tools for translating parameterizations of representations used during manual inspection to representation parametrizations usable by the representation generator.

In the simplest application of the discussed method, a user can select multiple representations or representation parametrizations that he considers to be relevant for a certain task that is equivalent or related to the determination of the output parameter or parameters. At least one embodiment of the inventive method can then be used to recognize superfluous representations that might not add additional information and avoid using these superfluous representations, therefore allowing for a lower complexity of the processing algorithm. Additionally or alternatively, the method can highlight representations that are considered to be most important and e.g. provide feedback concerning the importance of the representations to a user.

Additionally or alternatively, the method can slightly modify the representation parametrizations as discussed above based on the approximate representation parametrization, therefore potentially further improving the determination of the parameter or parameters.

At least one embodiment of the inventive method can especially be used to combine the experience of multiple practitioners. It is e.g. possible that the representation information collects predefined representation parametrizations that correspond to representations or combinations of representations that were considered to be relevant for a specific task by multiple users. At least one embodiment of the inventive method can then pick and optionally modify the representation or a combination of representations that is actually most suitable to determine the output parameter.

In the simplest case, all of the predefined representation parametrizations based on the user input by different users can be combined in a common pool and therefore arbitrary combinations and selections of these representation parametrizations can be used. To allow for a faster convergence of the optimization algorithm and a more reliable convergence, even when using relatively small training datasets, it can be advantageous to focus the sampling of the predefined representation parametrizations on combinations that were actually suggested by a single user. It is e.g. possible to first compare the performance of the different combinations suggested by the different users and then modify the most successful combination or combinations, e.g. by removing individual representation parametrizations to reduce the complexity and/or by replacing individual representation parametrizations by representation parametrizations based on the input of other users. These steps can be automatically performed by the proposed system and method. Once an optimum combination of the predefined representation parametrizations is found, this combination can then be further modified as discussed above.

The representation generator used in at least one embodiment of the inventive method allows for an automatic generation of representations for a given representation parametrization that can e.g. define certain slices or projections or different representations in an anatomical coordinate system. Besides the use of this representation generator within the optimization algorithm and the trained function such a representation generator provides multiple added advantages. For the individual user it is e.g. possible to generate the same representation for a multitude of medical image datasets, e.g. for different patients. This can allow for an easier comparison of the features in certain patients, the direct observation of changes of a patient over time, etc. It can also speed up the workflow of a manual determination of certain features, when the relevant representations can be automatically generated.

A further advantage of using such a representation generator to define representations via the representation parametrization is, that representation parametrizations can easily be exchanged between several users. This can be relevant for a manual analysis of medical image datasets, since a user can e.g. provide the representation parametrizations for the most relevant representations for a certain problem to another user, thereby assisting that user to analyze such medical image datasets. An exchange of representation parametrizations also increases the usefulness of at least one embodiment of the inventive method, since partial pools of used representation parametrizations can be provided by different users as already discussed above.

It is even possible to execute the optimization algorithm for a fixed set of a representation parametrizations. This can be advantageous to determine an optimum measure of performance for the processing algorithm when a given set of representation parametrizations is used. This procedure can e.g. be used to select between sets of representation parametrizations provided by different users, therefore only taking the most promising sets into consideration. It can also be used to provide a feedback to the individual user, providing the user with information on how suitable the selected representations were in general for determining a relevant feature.

A further advantage of the use of a representation generator and therefore the definition of representations by a respective representation parametrization is, that medical practitioners can share information concerning the used representations for a certain task without sharing the medical image data itself. It is e.g. sufficient to use the representation generator to generate representation during a manual evaluation of medical image datasets and to share the representation parametrizations to allow for these suggested representation parametrizations or sets of respective representation parametrizations to be used in at least one embodiment of the inventive method. The actual image data or any further patient data that was analyzed while defining these representation parametrizations does not need to be shared and can e.g. not leave the database of a hospital.

The sharing of the representation parametrization or parametrizations does however still allow for the intuition of the practitioner, e.g. of a radiologist, to be shared with colleagues and to be used to determine optimum representations as input for the processing algorithm in at least one embodiment of the inventive method. Since only the information concerning the generation of the representation is shared, the privacy of the individual patient is optimally protected. At the same time, a medical expert, e.g. a radiologist, working with the representation generator or a tool kit for image representation comprising the representation generator would not need in depth technical knowledge and could still provide valuable information, mainly candidate representation parametrizations, for at least one embodiment of the inventive method simply by using such a tool kit or representation generator to generate representations during his normal work and optionally mark representations or groups of representations that he considers to be especially relevant.

The optimization algorithm can use a pool of potential representation parametrizations defined by the representation information, wherein for at least a selected one of the representation parametrizations in the pool a measure of the relevance of the selected representation parametrization is determined by comparing the optimum measure for the performance achieved in the optimization algorithm when using the selected representation parametrization to generate a training representation with the optimum measure for the performance achieved when not using the selected representation parametrization to generate training representations. The pool can e.g. initially be identical to the predefined representation parametrizations discussed above. The relevance can e.g. be sequentially determined for each of the representation parametrizations and the representation parametrization with the lowest determined relevance can be discarded to reduce the number of the representation parametrizations in the pool. This process can be repeated multiple times to reduce the pool to the most relevant representation parametrizations. These most relevant representation parametrizations can then e.g. be varied as discussed above to further improve the determination of the at least one output parameter.

The determined relevance for a respective representation parametrization can also be provided as feedback to a user. It is e.g. possible, that the user defines a certain number, e.g. five, representations that he considers to be relevant to determine the output parameter or parameters. The method can then provide feedback informing the user that e.g. one or two of his suggested representations have a low relevance and can e.g. actually not contribute relevant information for the determination of the output parameter or parameters. Such an approach can be relevant to not only train the function itself but also train the individual user in recognizing which representations might be relevant for determining certain parameters, e.g. diagnosis metrics and/or biomarkers.

The optimization algorithm can e.g. be an iterative algorithm, wherein each iteration comprises on the one hand the selection of a combination of the used representation parametrization or the used set of representation parametrizations and the used processing algorithm for this iteration, and on the other hand the optimization of the measure of performance by varying the algorithm parameters.

In principle, the selection of the processing algorithm and the representation parametrization or parametrizations could be random. To improve convergence in this case, representation parametrizations for which no or little relevance was determined as discussed above, could be discarded from the pool to avoid their use in further iterations.

It is however advantageous to take the results of previous iterations into account when selecting the representation parametrization or parametrizations and/or processing algorithm in a respective iteration. This can e.g. be achieved by using a Bayes optimization that select both the user representation parametrization or parametrizations and the processing algorithm. The Bayes optimization is well-known in the prior art and will not be discussed in detail. This approach is based on defining a so-called prior function containing assumptions about e.g. the dependence of the measure of the performance or a cost function on the position in the parameter space. This prior is updated after each sampling of the parameter space. The selection of the next sample depends on an acquisition function that can especially depend on the degree of uncertainty of the updated prior function in a given range and the closeness of the prior function to the expected maximum or minimum in this range. This approach can therefore combine the exploration of the parameter space, namely minimizing the uncertainty in unknown parts of the parameter space, and the exploitation, namely focusing the sampling on the neighborhood of the current best-known solution.

Alternatively, an evolutionary algorithm could be used to determine the representation parametrization or parametrizations and processing algorithm in each iteration of the optimization algorithm. In evolutionary algorithms promising parameter sets, e.g. promising combinations of representation parametrization or parametrizations and processing algorithm that show a good measure for the performance are selected and then combined and/or modified to provide parameter sets for the next iteration. Evolutionary algorithms are well-known in the prior art and will not be discussed in detail.

For pixels or voxels or groups of neighboring pixels or voxels of a respective representation of the medical image dataset defined by the respective determined representation parametrization, a measure of the influence of the respective pixel or voxel or group of neighboring pixels or voxels on the output parameter or at least one of the output parameters can be determined based on the determined processing algorithm and algorithm parameters. If the processing algorithm is differentiable, the gradient of the parameter with respect to the pixel, voxel or group of pixels or voxels can be determined and used as the measure for the influence. A color-coded image showing the influence of the respective pixel, voxel, or group on the parameter or parameters can then be generated and e.g. be visualized for a user. This can especially be relevant when the representation information is based on user input, e.g. on a selection of representations by a user deemed relevant to determine the output parameter or parameters.

The described approach determines a saliency map of the processing algorithm parametrized by the algorithm parameters and can therefore immediately provide feedback to the user which areas of a certain representation were relevant to determine the output parameter or parameters. Therefore, it can not only be determined, which representations are especially relevant, but also which areas of the representations are especially relevant. This approach can serve two purposes. On the one hand, it might actually provide new information to the user, which areas of certain representations might be relevant for certain diagnostic problems. On the other hand, such a mapping of the relevance of the pixels, voxels or groups can serve to validate the training, since the user can instantly recognize when certain areas are considered to be highly relevant that should have no connection with the parameter or parameters determined. While this might indicate new medical knowledge, it might also be caused by an interpretation of an artefact as a feature or similar problems. Potential pitfalls of machine learning due to the black box nature of trained functions can therefore easily be recognized and avoided.

At least one embodiment of the invention also concerns a method for evaluating medical image data, comprising the steps:
  receiving a medical image dataset concerning a region of interest as input data,
  applying a function trained by a machine learning algorithm to the medical image dataset to determine at least one output parameter, wherein the function comprises a processing algorithm determined and/or parametrized by machine learning and a representation generator, wherein the representation generator generates at least one representation of the region of interest based on the medical image dataset and a respective representation parametrization determined by machine learning, and wherein the processing algorithm determines the output parameter based on the at least one representation,
  providing the output parameter as output data.

The used representation parametrization or parametrizations and the used processing algorithm can be provided by the computer-implemented method for parameterizing the function discussed above. It is possible that a completely trained processing algorithm is provided, in which the previously discussed algorithm parameters are hardcoded. It is however also possible to separately provide the processing algorithm and its parameters.

Additionally, at least one embodiment of the invention concerns a providing system comprising
  a first interface, configured for receiving input data,
  a second interface, configured for providing output data,
  a computation unit, configured
    to determine the at least one determined representation parametrization and the determined processing algorithm or parameters describing the determined processing algorithm as the output data based on the training dataset and the representation information as input data according to the computer-implemented method for parameterizing a function, and/or
    to determine the output parameter as output data based on the medical image dataset as input data according to the computer-implemented method for evaluating medical image data.

A computer program according to at least one embodiment of the present invention comprises instructions which, when the computer program is executed by a computer, causes the computer to carry out the computer-implemented method for parameterizing a function according to at least one embodiment of the present invention and/or the computer-implemented method for evaluating medical image data according to at least one embodiment of the present invention.

A computer-readable medium according to at least one embodiment of the present invention comprises a computer program according to at least one embodiment of the present invention.

The discussed group of embodiments of inventions allows for using the intuition and knowledge of medical experts, especially when the representation information is defined based on user inputs. It also allows for providing the users with feedback concerning the relevance of the selected representations and about the areas of the representations that are especially relevant concerning the determination of the output parameter or parameters. It therefore provides a workflow to medical practitioners that is similar to their typical research, namely a workflow that allows for them to define a certain hypothesis concerning the relevance of certain representations of medical image datasets for the determination of certain parameters and to test the respective hypothesis namely by providing them feedback concerning the relevance of the different representations and the relevant regions.

At the same time the medical practitioners do not need detailed technical knowledge to provide the relevant information for parametrizing the function for evaluating a medical image dataset, since they can simply use the representation generator or a toolkit comprising the representation generator to generate representations in their normal workflow. Their expert knowledge can also be shared without sharing the medical image dataset and therefore without sharing any personal information concerning the patient.

The representation generator can be provided as a toolbox to medical examiners independent of the discussed methods and systems or as part of these methods and systems. It can comprise e.g. unfolding algorithms, algorithms for generating curved planar representations, multi-planar reformatted representations, reparameterizations, e.g. based on polar coordinates starting from the center of mass, variants of histogram equalization, anatomical coordinate systems, etc. The selection of the used algorithm and the parameters of the algorithm can then be stored as representation parametrization for the generated representation. Representations flagged as potentially discriminative for the relevant output parameter or parameters can be automatically propagated to all other patients of a study by applying the representation generator using the same representation parametrization. These representations can then be stored in the representation pool and be directly drawn during the optimization algorithm. Alternatively, the representations could be generated on the fly within the optimization algorithm.

A major advantage of the discussed approach is the ability to simultaneously optimize the used representations or representation parametrizations used to generate the representations and the architecture of a deep learning network by choosing the processing algorithm from the search space. During this optimization advanced performance estimation and optimization strategies can be used. An overview of strategies that could be used is given by the already cited paper by T. Elsken et al. Since representations and neural architectures are searched at the same time, the proposed method could be called data representation and neural architecture search (DaReNAS).

Representations suggested by the user that turn out to be non-relevant for the decision of the system or method can automatically be rejected. The system can therefore be interpreted as an abstract, image-based version of an univariate hypothesis test. Since feedback is provided, it can also school the radiological intuition for maximum informational content.

As previously discussed, the non-rejected representations can then be refined and the effect of the adjustments can be evaluated to further improve the determination of the output parameter or parameters.

When the representation information is based on user input, especially based on representations suggested by users, it also improves interpretability of the generated output parameter or parameters, since these parameters are based on representations that are also used by medical experts when working on the same diagnostic problem or related problems. If e.g. the saliency map is provided as discussed above, it is easy to understand for such experts what features drive the trained function to its conclusion and therefore to the provided output parameter or parameters.

The interaction with the user, e.g. a radiologist, could be further improved, e.g. by recommending representations or representation parametrizations in a new study that were considered relevant in previous studies.

FIG. 1 shows a flowchart of a computer-implemented method for evaluating medical image data. A possible implementation of the shown steps S1-S4 will be discussed with additional reference to FIG. 2 that shows relevant algorithms and data structures usable to implement the method.

In step S1 a medical image dataset 1 concerning a region of interest is received as input data 2. The input data 2 can be directly provided by a medical image acquisition device, e.g. a CT- or MRT-device, be read from a database, etc. The examples will assume that the medical image dataset 1 describes three-dimensional image data. The described methods and devices could however also be used to process two-dimensional image data.

In steps S2 and S3 a function 3 trained by machine learning is applied to the medical image dataset 1 to determine at least one output parameter 4. The process of training the function 3 is later discussed with reference to FIGS. 3 and 4 and can be considered to be a preparatory step that is separate from the discussed method.

The function 3 comprises two distinct processing steps. In step S2 a representation generator 6 is used to generate at least one, preferably several, representations 7 of the region of interest depicted in the medical image dataset 1. The representations 7 can e.g. be different slices of the volume depicted in the medical image dataset 1, projection images, e.g. generated by performing an artificial x-ray projection of the medical image dataset 1, multiplanar reformatted representations, curved planar reformations, unfolded representations of the region of interest, etc. The type of the respective representation 7 and further parameters of the representation 7, e.g. the angle and/or position of a slice or the projection direction of a projection image are defined by a respective representation parametrization 8. The determination of the representation parametrizations 8 is part of the training of the function described later with reference to FIGS. 3 and 4 and can be considered to be a preparatory step that is separate from the discussed method.

In step S3 the output parameter 4 is determined by a processing algorithm 5 that is previously determined and/or parametrized by machine learning. The determination and parametrization of the processing algorithm 5 is part of the training of the function that will later be described with reference to FIGS. 3 and 4 and can be considered to be a preparatory step that is separate from the discussed method.

Preferably, the selected processing algorithm 5 only describes a neural architecture, e.g. the connections between nodes and/or layers of neural networks and operations performed in individual convolutional layers and/or activation functions of individual nodes. The parameters typically determined in machine learning, e.g. input weights of individual nodes and/or filtering kernels of convolution layers, can be provided separately as algorithm parameters 10. Alternatively, the algorithm parameters 10 could already be hardcoded in the processing algorithm 5 itself.

Instead of selecting a processing algorithm with a given architecture from a search space, it would also be possible to use a generic processing algorithm 5 that can implement a multitude of architectures and chose the architecture by providing processing parameters 9 determined by machine learning.

Once the output parameter 4 is determined, it can be provided as output data 11 in step S4. The output data 11 can e.g. be used to support medical personnel in forming a diagnosis. E.g. a probability of the presence of certain features indicating a disease could be provided as output parameter 4.

While most approaches to machine learning use a fixed representation and neural architecture and only vary the parameters, e.g. input weights of artificial neutrons, during machine learning and more advanced approaches use neural architecture searches based on fixed representations as input data, the proposed method allows a variation of the used representations and neural architectures during the machine learning. To still allow for the learning process to work with limited amounts of training data and computational resources, the search space for the used representations can be limited by using representations suggested by users as a starting point and therefore by levering the intuition of medical practitioners.

This approach is implemented in that the discussed method uses at least one representation 7 as input for the processing algorithm 5 that is generated by the representation generator 6 based on a representation parametrization 8 that is provided based on machine learning. The discussed method therefore allows for learning a suitable representation to determine the output parameter 4. E.g. a relatively small number of two-dimensional images can be used as representations 7, therefore reducing the amount of input data compared to a processing of the full volume of three-dimensional image data provided by the medical image dataset 1.

Since the use of different representations 7 as input data might require different architectures of the processing algorithm 5 for optimum performance, the architecture of the processing algorithm 5 is also determined using machine learning.

The combination of these features allows for a reduction of the amount of input data processed to determine the output parameter 4 and therefore of the complexity of the processing algorithm 5 and especially of the number of algorithm parameters 10 that need to be determined during the training. This can notably reduce the amount of necessary training data and lead to a better performance of the function 3 compared to algorithms that use a fixed set of representations during training.

Figure 3:
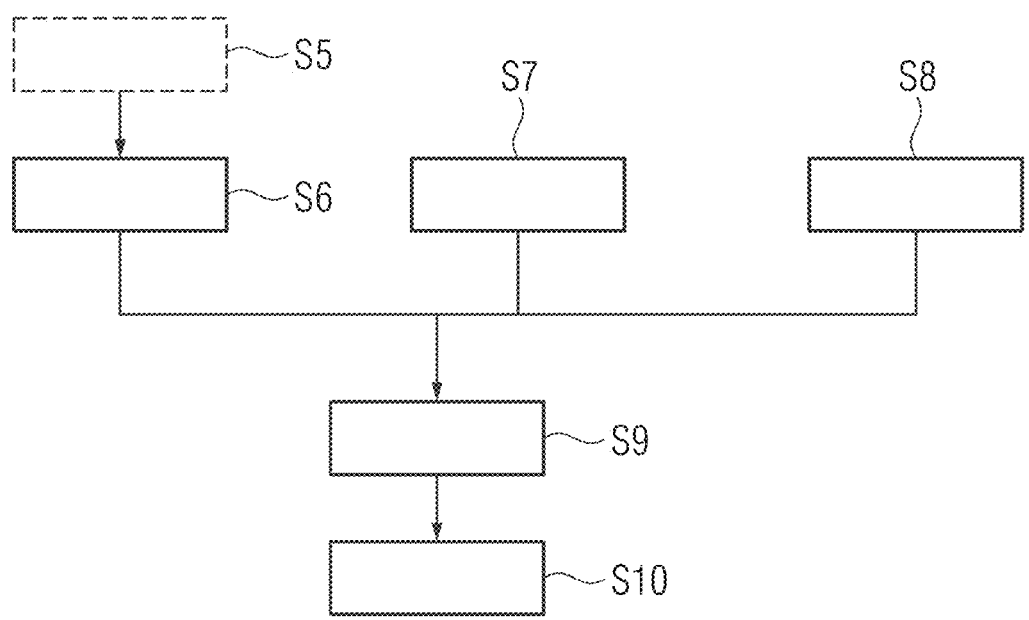
Figure 4:
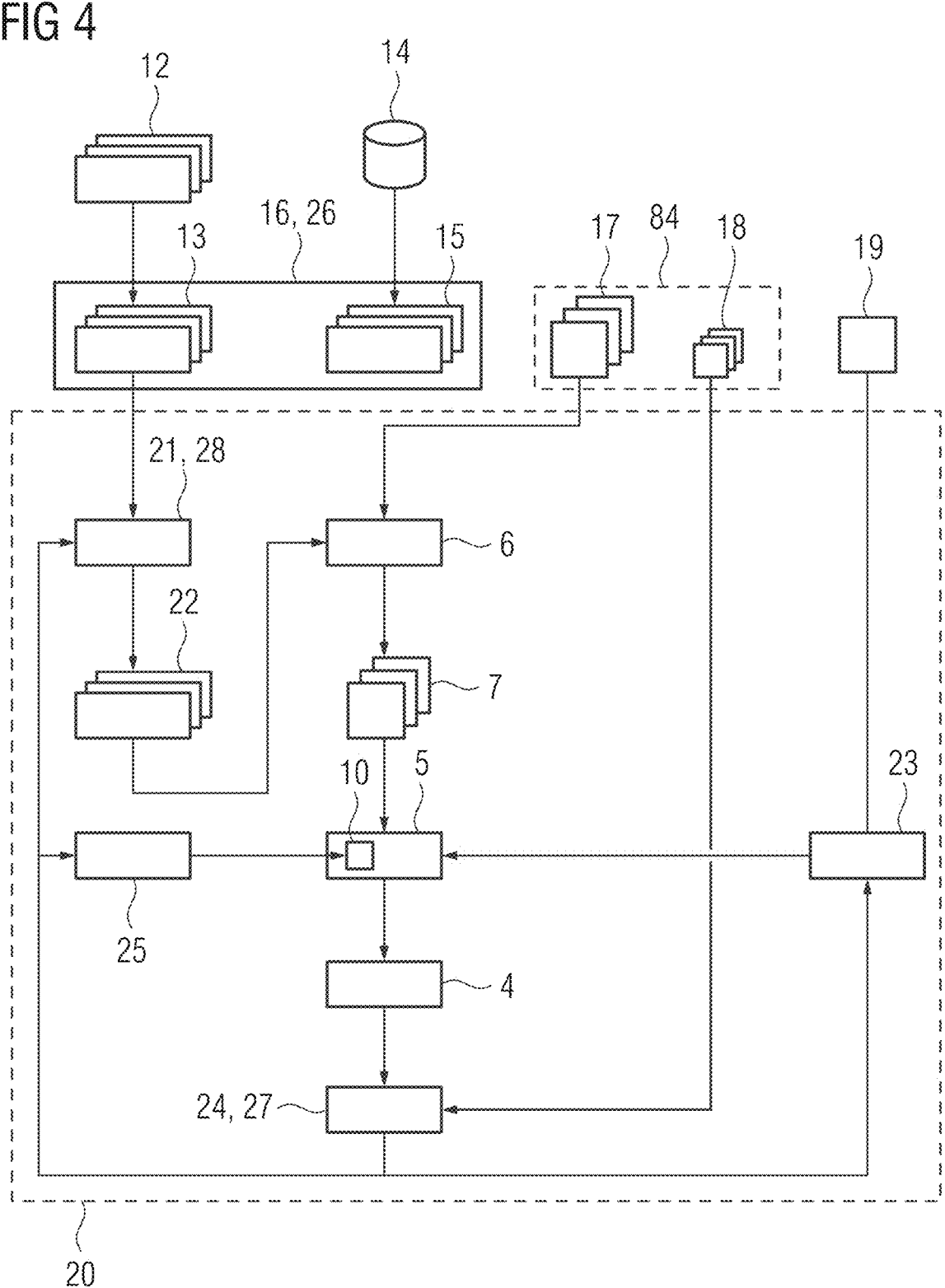

An example for a computer-implemented method for parametrizing the function 3 will now be discussed with reference to FIGS. 3 and 4. FIG. 3 shows a flowchart of method and FIG. 4 shows relevant data structures and algorithms for a possible implementation of this method.

In a first optional step S5, user input 12 is received from a user concerning the selection of representations 7 that the user considers to be relevant for the determination of the output parameter 4 or for a diagnostic task related to the output parameter 4. It is e.g. possible that the user is using a tool kit to generate representations 7 from a medical image dataset 1 that uses the previously discussed representation generator 6 to generate the individual representations 7. Taking such user inputs and especially predefined representation parametrizations 13 generated from these user inputs into account when selecting suitable representations 7 as input data for the processing algorithm 5 allows for the use of the experience of medical experts to train the function 3.

In step S6 representation information 16 is received that can comprise the predefined representation parametrizations 13 determined from the user input 12 and/or predefined representation parametrizations 15 received from a different source 14, e.g. a database, a different user, etc.

In step S7 a training dataset 84 is received comprising multiple training medical image datasets 17. Since the discussed example uses supervised learning, the training dataset 84 additionally comprises desired values 18 for each training medical image dataset 17 and output parameter 4.

In step S8 a search space 19 is defined for the network architectures of the processing algorithm 5. For example, the search space 19 could be limited to convolutional neural networks comprising repeated cells within identical architecture.

It is e.g. possible to form the processing algorithm 5 by an alternate use of normal cells that are applied with a stride of one, therefore keeping the amount of output data the same as the amount of input data, and reduction cells that are applied with a stride of two, therefore reducing the amount of output data by the factor of two. All normal cells can have the same network architecture and all reduction cells can have the same network architecture, that is preferably different from the architecture of the normal cells. In this context having the same architecture can mean using the same operations on a respective convolutional layer and using the same connections between the layers within the respective cell.

Examples of such network architectures are given in the previously cited paper by H. Pham et al, the entire contents of which are hereby incorporated herein by reference. This paper and especially the previously cited paper by T. Elsken et al., the entire contents of which are hereby incorporated herein by reference, also suggest further search spaces that could be used instead of the discussed search space 19.

In step S9 an optimization algorithm 20 is used to determine the processing algorithm 5 and at least one representation parametrization 22 that is expected to provide the optimum performance of the processing algorithm 5. To clearly illustrate the relevant ideas a relatively simple embodiment of the optimization algorithm 20 is schematically shown in FIG. 4 that uses an explicit iteration over various processing algorithms 5 drawn from the search space 19 and representation parametrizations 22 drawn from a pool 26 defined by the representation information 16, wherein a complete training of the processing algorithm 5 is performed during each iteration to determine the algorithm parameters 10. While such an approach is in principle possible, a real-world implementation would typically use several modifications to speed-up the convergence of the training process that will be discussed later.

Figure 2:
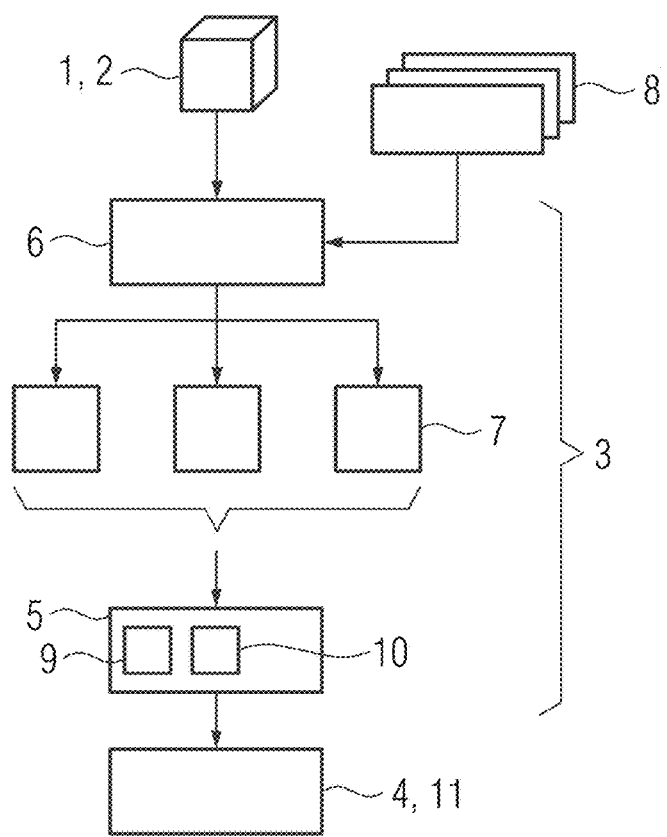

In the optimization algorithm 20 shown in FIG. 4 a selection module 21 selects a sub-set of the representation parametrizations 22 from the pool 26 of representation parametrizations 13, 15 defined by the representation information 16. The representation generator 6 already discussed with reference to FIG. 2 is then used to generate a respective representation 7 for each of the selected representation parametrizations 22 for at least some of the training medical image datasets 17. In an alternate embodiment it would also be possible to already generate representations 7 for all the representation parametrizations 13, 15 in the pool 26 and then use the selection module 21 to directly select one of the representations 7.

A processing algorithm 5 selected from the search space 19 by the selection module 23 is then trained by using these representations 7 as input data. The algorithm parameters 10 of the processing algorithm 5, e.g. the input weights of the individual nodes of a neural network or filter kernels of a convolutional neural network, can initially be set to random values or some selected default values. Using this parametrization, the processing algorithm 5 is then applied to the input data, namely the representations 7, to generate the output parameter 4. The output parameter 4 is compared to the desired value 18 for the output value, e.g. using a cost function 24. Depending on the value of the cost function 24, especially depending on the difference between the generated output parameter 4 and the desired value 18, the algorithm parameters 10 are then modified by a modification module 25 that could e.g. use a back-propagation of error or some other well-known method for training an algorithm 5 by machine learning.

After a certain amount of training the value of the cost function 24 is determined as the measure 27 of the performance of the processing algorithm 5 when operating on the representations 7. In the next step of the iteration, the processing algorithm 5 is redrawn from the search space 19 and/or the subset of representation parametrizations 22 or representations 7 is redrawn from the pool 26 to check if the measure 27 for the performance can be improved for this new combination.

In principle it would be possible to randomly select the processing algorithm 5 from the search space 19 and/or the selected representation parametrizations 22 from the pool 26. To speed up the parametrization of the function 3 it is however advantageous to take the previous results, especially the determined measures 27, into consideration when selecting new representation parametrizations 22 or representations 7 and/or processing algorithms 5. This could e.g. be achieved by using an evolutionary algorithm or an acquisition function in a Bayes optimization for the selection in the selection modules 21, 23.

Additionally or alternatively, the pool 26 could be modified by removing representation parametrizations 13, 15 that are determined to have no or little relevance for the determination of the output parameter 4. This can e.g. be determined by comparing the optimum measure 27 for the performance achieved in the optimization algorithm 20 when using the selected representation parametrization to generate the training representations 7 with the optimum measure 27 for the performance achieved when not using the selected representation parametrization to generate training representations 7.

Once the subset with the optimum performance is found, the selection of a new subset by the selection module 21 can be replaced by a modification 28 of the parameters of the selected representation parametrizations. E.g. the position and/or orientation of the selected slice for a given representation 7 and/or the direction of a projection could be slightly modified and it could be checked if further improvements of the performance can be achieved by this modification.

Once the optimization is complete, e.g. after a certain number of iterations or when a conversion criterion is fulfilled, the determined processing algorithm 5 or processing parameters 10 describing the processing algorithm 5 and the determined representation parametrizations 22 can be provided as output, therefore enabling the method already discussed with reference to FIGS. 1 and 2.

The previously discussed approach in which a complete training of the processing algorithm 5 is performed for each set of representation parametrizations 22 and selected processing algorithm 5 is quite computationally expensive. Since the core reason for the computational hardness is the complex neural architecture search, various approaches to optimize such neural architecture searches known from the prior art can be used to speed up the training of the function 3.

A promising approach is the use of one-shot models and weight sharing in which each member of the search space 19 can be considered to be a sub-graph of a graph describing an overall network. It is therefore sufficient to train the overall network that is also called one-shot model. An example of such one-shot models that is well-suited for the discussed problem is the ENAS model discussed in detail in the previously cited document by Pham et el. Additional approaches for reducing the complexity of the neural architecture search are low fidelity estimates, learning curve extrapolation and weight inheritance. These approaches are discussed in the previously cited article by Elsken et al.

Figure 5:
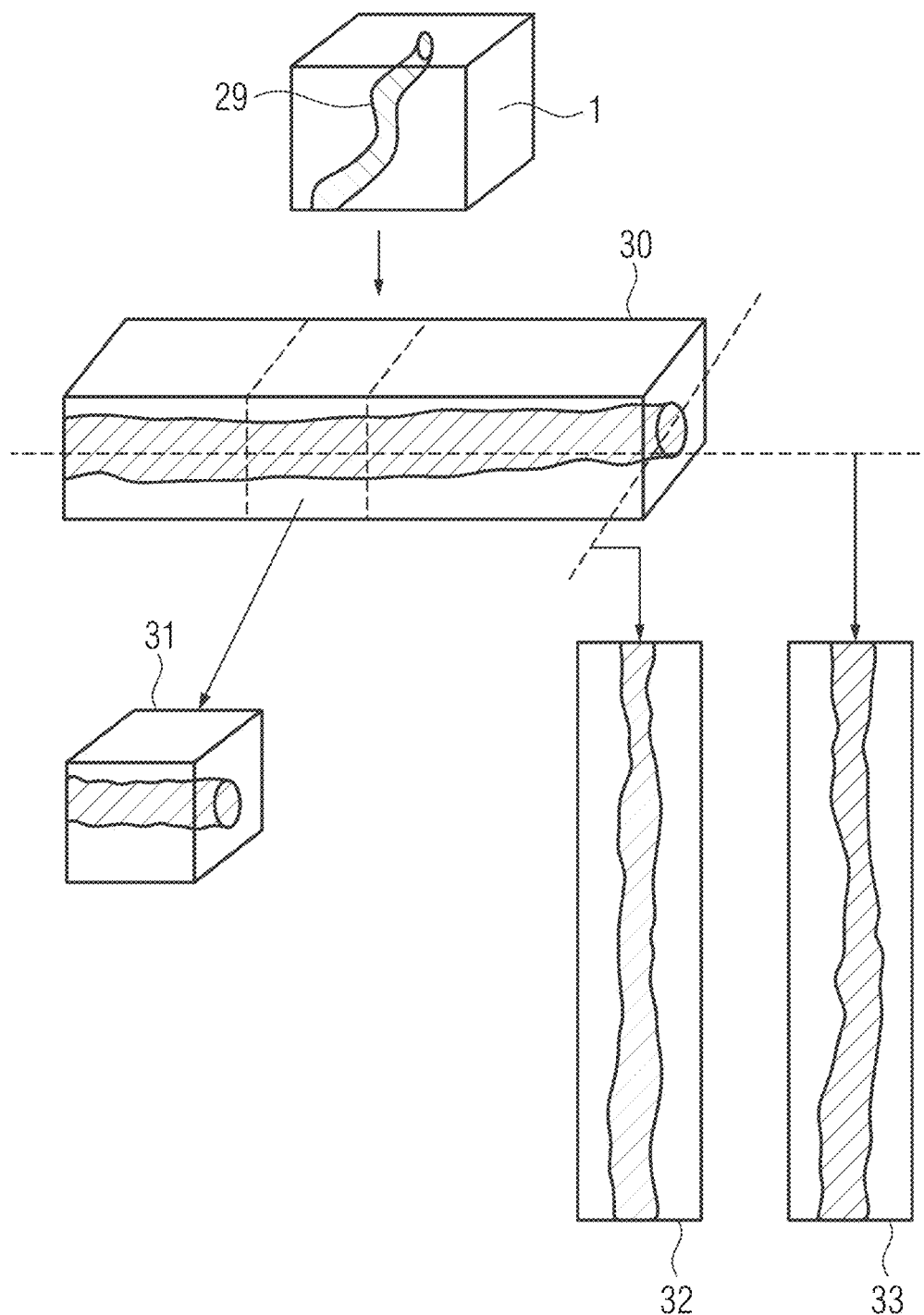

FIG. 5 shows a few example representations 30, 31, 32, 33 of a region of interest 29 depicted in a medical image dataset 1. The selection of the shown representations is inspired by the paper by Danzinger et al., the entire contents of which are hereby incorporated herein by reference, that was already cited. All shown representations are based on a first step in which the region of interest 29, e.g. a vessel or lesion, is reshaped into a multi-planar reformatted image stack that is shown as representation 30 in FIG. 5. Such a multi-planar reformatted image stack can be formed by creating interpolated planes orthogonal to the centerline of the vessel or lesion that forms the region of interest 29 and stacking them, therefore essentially straightening the region of interest 29.

The representation 30 therefore already contains noticeably less information that is not related to the region of interest 29, since it only needs to extend slightly beyond the region of interest 29. Processing the full representation 30 at full resolution would however still require a rather complex processing algorithm. Therefore, the cited paper tests various further representations. One possible representation 31 is the use of smaller cubes spaced along the region of interest 29. Further representations 32, 33 can be created by selecting certain slices, in an example orthogonal slices comprising the centerline of the region of interest 29, as input data for the processing algorithm. Additionally, a multitude of further representations would be possible, e.g. directly selecting slices from the medical image dataset 1, using projections of the medical image dataset 1 or of the representation 30, further processing the volumetric images of the representations 31, e.g. by creating projections or by selecting certain slices, etc. Projections could be artificial x-ray images or minimum or maximum intensity projections.

The cited paper manually examined a few possible sets of input representations and compared the performance of the used processing algorithm for these representations. It arrived at the conclusion that the use of the representations 32 and 33 as input data seems to yield optimum results. The previously discussed method would find suitable representations with noticeably less effort and could potentially further improve the performance by sampling other representations and also combinations of certain representation, e.g. by combining one of the representations 32, 33 with the projection of the full medical image dataset 1 or some other combination that might not be immediately obvious. Therefore, the discussed method also allows the discovery of optimized solutions that will probably not be discovered when hand-crafting the neural architecture and especially manually selecting the representations to be used.

The discussed representations are advantageous for e.g. the field of cardiology, especially for characterizing coronary arterial plaque segments, which can narrow the vessel and lead to a stroke and adverse myocardial events. In other fields, e.g. for supporting medical personnel in forming a diagnosis concerning a lung disease, other representations might be advantageous.

For a detection of indicators for the presence of chronic obstructive pulmonary disease it might be sufficient to use a simple 2D overview image, e.g. a projection at a certain angle, as input data for the processing algorithm. Indicators for pulmonary diseases correlating with inflammatory processes manifest as a thickening of their walls and might be well visualized in multi-planar reformatted image stacks. Therefore, similar representations might be used that were already discussed with respect to FIG. 5. Other useful representations might be a curved planar reformation or the output of an unfolding algorithm.

It is therefore advantageous when the representation generator 6 comprises a multitude of algorithms for generating the representations 7 and can therefore be used for a multitude of image analysis problems in medical imaging. The search space for relevant representations and therefore relevant representation parametrizations can be limited by the representation information. As previously discussed, it is especially advantageous to collect information from one or multiple medical experts concerning representations or combinations of representations that might be advantageous for a certain image analysis task and therefore for the determination of a certain output parameter or a group of output parameters.

Therefore, the method can be applied to a multitude of image analysis tasks simply by determining, what representations might be relevant, e.g. by tracking the usage of a representation generator by a medical expert during a manual determination of respective output parameters or during diagnostic tasks related to these output parameters.

An illustration of a possible search space 19 for the processing algorithm 5 will now be discussed with reference to FIG. 6. In the example the search space is limited to convolutional neural networks that are formed by an input layer 34, multiple sequential cells 35, 36, each cell comprising a multitude of layers 38-40, and an output layer 73 that can e.g. be formed by a fully connected layer. The cells 35, 36 can have different architectures from each other and this sequence of cells 35, 36 is repeated multiple times to form the respective processing algorithm 5. The cell 35 can be a normal convolutional cell, e.g. a cell that uses the stride of one for a convolutional kernel and therefore generates output data having the same resolution as the input data. The cell 36 can be a reduction cell with an increased stride, e.g. a stride of two, that will therefore generate output data at a decreased resolution.

Figure 6:
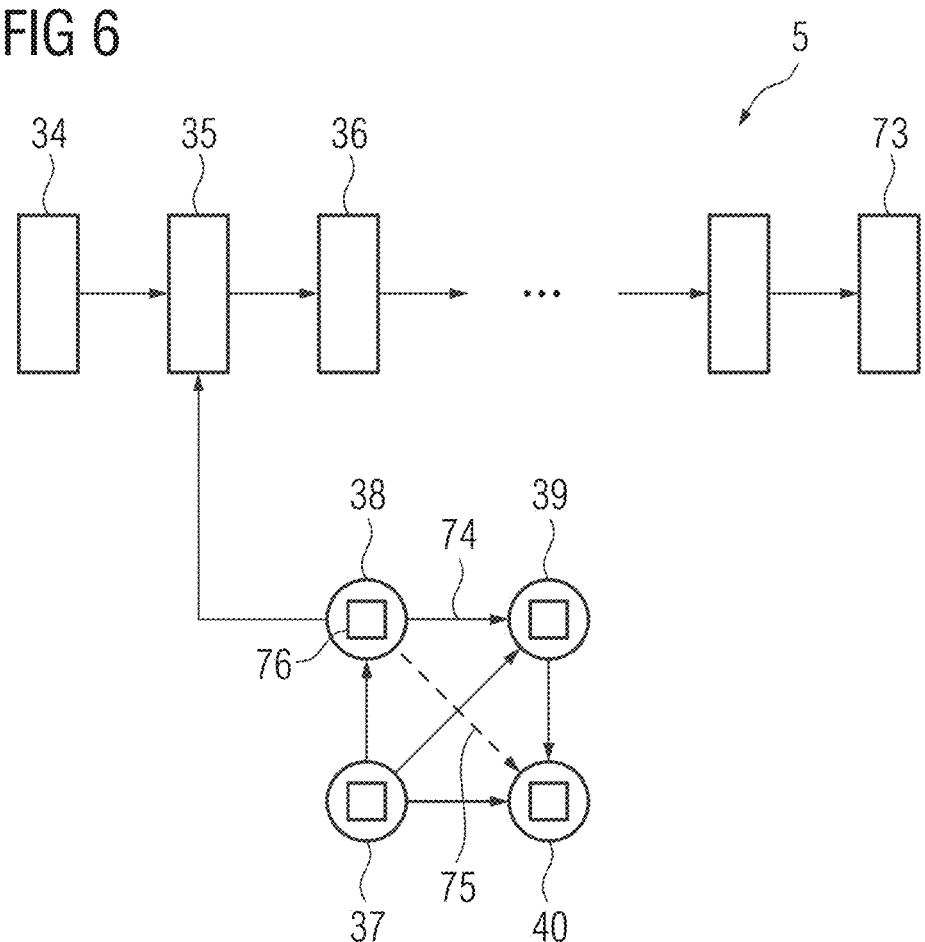

FIG. 6 shows a very simple example of such a search space in which the number of layers 38-40 of each of the cells 35 is limited to four. The different processing algorithms 5 within the search space differ concerning the architecture of the normal cell 35 and the reduction cell 36. This architecture defines which connections 74, 75 are present between the convolutional layers 38-40. In FIG. 6 all possible connections 74, 75 are shown as arrows, wherein the used connections 74 are shown as solid arrows and the one connection 75 that is not used in the example is shown as a broken arrow.

As shown in FIG. 6 the final layer 40 in the cell 35 can have potential connections 74, 75 to all previous layers 37-39. In the example only the connections to the previous layers 37 and 39 are used, such that the example for the processing algorithm 5 as shown in FIG. 5 does not directly use the output of the layer 38 as input for the layer 40. When potentially allowing connections of each layer 37-40 to each of the previous layers 37-40 in the same cell 35 there are six potential connections and therefore 26 possibilities for the architecture concerning the connections between the different layers 37-40.

The architecture of the processing algorithm 5 can also define the type of the operation 76 performed by the respective layers 37-40. A certain layer can e.g. perform a maximum pooling, minimum pooling, average pooling, convolution, depth wise separable convolution or output an identity. The architecture can also define the size of the used kernel, e.g. select between a 3×3 and 5×5 kernel.

The previous discussion can also be transferred to search spaces for different neural networks. Instead of connections between conversional layers 37-40 connections between individual nodes can then be defined by the architecture and the selection between different types of operations 76 can be replaced by selection of the used activation function, e.g. by a choice between a tank, ReLU, identity or sigmoid functions.

As technical background for the invention the general principals and structure of neural networks and especially convolutional neural networks will now be discussed with reference to FIGS. 7 and 8.

Figure 7:
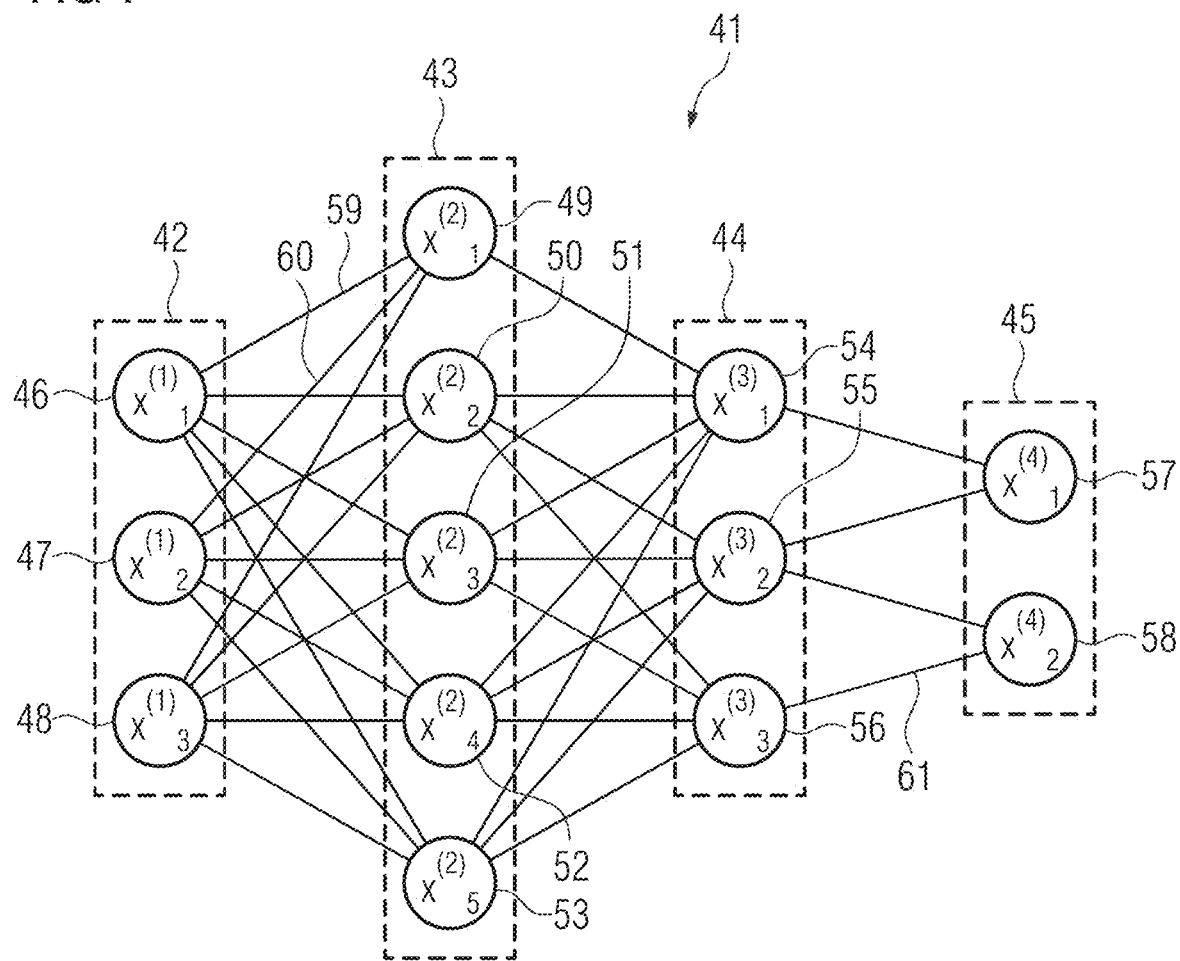

FIG. 7 displays an embodiment of an artificial neural network 41. Alternative terms for "artificial neural network" are "neural network", "artificial neural net" or "neural net".

The artificial neural network 41 comprises nodes 46-58 and edges 59-61 wherein each edge 59-61 is a directed connection from a first node 46-48 to a second node 46-58. In general, the first node 46-58 and the second node 46-58 are different nodes 46-58, it is also possible that the first node 46-58 and the second node 46-58 are identical. For example, in FIG. 1 the edge 59 is a directed connection from the node 46 to the node 49, and the edge 60 is a directed connection from the node 47 to the node 49. An edge 59-61 from a first node 46-58 to a second node 46-58 is also denoted as "ingoing edge" for the second node 46-58 and as "outgoing edge" for the first node 46-58.

In this embodiment, the nodes 46-58 of the artificial neural network 41 can be arranged in layers 42-45, wherein the layers 42-45 can comprise an intrinsic order introduced by the edges 59-61 between the nodes 46-58. In particular, edges 59-61 can exist only between neighboring layers of nodes 46-58. In the displayed embodiment, there is an input layer 42 comprising only nodes 46-48 without an incoming edge, an output layer 45 comprising only nodes 57, 58 without outgoing edges, and hidden layers 43, 44 in-between the input layer 42 and the output layer 45. In general, the number of hidden layers 43, 44 can be chosen arbitrarily. The number of nodes 46-48 within the input layer 42 usually relates to the number of input values of the neural network, and the number of nodes 57, 58 within the output layer 45 usually relates to the number of output values of the neural network.

In particular, a (real) number can be assigned as a value to every node 46-58 of the neural network 31. Here, $x^{(n)}_i$ denotes the value of the i-th node 46-58 of the n-th layer 42-45. The values of the nodes 46-48 of the input layer 42 are equivalent to the input values of the neural network 41, the values of the nodes 57, 58 of the output layer 45 are equivalent to the output value of the neural network 41. Furthermore, each edge 59-61 can comprise a weight being a real number, in particular, the weight is a real number within the interval [−1, 1] or within the interval [0, 1]. Here, $w^{(m,n)}_{i,j}$ denotes the weight of the edge between the i-th node 46-58 of the m-th layer 42-45 and the j-th node 46-58 of the n-th layer 42-45. Furthermore, the abbreviation $w^{(n)}_{i,j}$ is defined for the weight $w^{(n,n+1)}_{i,j}$.

In particular, to calculate the output values of the neural network 41, the input values are propagated through the neural network. In particular, the values of the nodes 46-58 of the (n+1)-th layer 42-45 can be calculated based on the values of the nodes 46-58 of the n-th layer 42-45 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 42 are given by the input of the neural network 41, wherein values of the first hidden layer 43 can be calculated based on the values of the input layer 42 of the neural network, wherein values of the second hidden layer 44 can be calculated based in the values of the first hidden layer 43, etc.

In order to set the values $w^{(m,n)}_{i,j}$ for the edges, the neural network 41 has to be trained using training data. In particular, training data comprises training input data and training output data (denoted as ti). For a training step, the neural network 41 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 41 (backpropagation algorithm). In particular, the weights are changed according to $$w'^{(n)}_{i,j} = w^{(n)}_{i,j} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

the (n+1)-th layer is the output layer 45, wherein f' is the first derivative of the activation function, and $y^{(n+1)}$ is the comparison training value for the j-th node of the output layer 45.

FIG. 8 displays an embodiment of a convolutional neural network 62. In the displayed embodiment, the convolutional neural network 62 comprises an input layer 63, a convolutional layer 64, a pooling layer 65, a fully connected layer 66 and an output layer 67. Alternatively, the convolutional neural network 62 can comprise several convolutional layers 64, several pooling layers 65 and several fully connected layers 66 as well as other types of layers. The order of the layers can be chosen arbitrarily, usually fully connected layers 66 are used as the last layers before the output layer 67.

In particular, within a convolutional neural network 62 the nodes 68-72 of one layer 63-67 can be considered to be arranged as a d-dimensional matrix or as a d-dimensional image. In particular, in the two-dimensional case the value of the node 68-72 indexed with i and j in the nth layer 63-67 can be denoted as $x^{(n)}[i,j]$. However, the arrangement of the nodes 68-72 of one layer 63-67 does not have an effect on the calculations executed within the convolutional neural network 62 as such, since these are given solely by the structure and the weights of the edges.

In particular, a convolutional layer 64 is characterized by the structure and the weights of the incoming edges forming a convolution operation based on a certain number of kernels. In particular, the structure and the weights of the incoming edges are chosen such that the values $x^{(n)}_k$ of the nodes 69 of the convolutional layer 64 are calculated as a convolution $x^{(n)}_k = K_k * x^{(n-1)}$ based on the values $x^{(n-1)}$ of the nodes 68 of the preceding layer 63, where the convolution is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 68-72 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 68-72 in the respective layer 63-67. In particular, for a convolutional layer 64 the number of nodes 69 in the convolutional layer is equivalent to the number of nodes 68 in the preceding layer 63 multiplied with the number of kernels.

If the nodes 68 of the preceding layer 63 are arranged as a d-dimensional matrix, using a plurality of kernels can be interpreted as adding a further dimension (denoted as "depth" dimension), so that the nodes 69 of the convolutional layer 64 are arranged as a (d+1)-dimensional matrix. If the nodes 68 of the preceding layer 63 are already arranged as a (d+1)-dimensional matrix comprising a depth dimension, using a plurality of kernels can be interpreted as expanding along the depth dimension, so that the nodes 69 of the convolutional layer 64 are arranged also as a (d+1)-dimensional matrix, wherein the size of the (d+1)-dimensional matrix with respect to the depth dimension is by a factor of the number of kernels larger than in the preceding layer 63.

The advantage of using convolutional layers 64 is that spatially local correlation of the input data can exploited by enforcing a local connectivity pattern between nodes of adjacent layers, in particular by each node being connected to only a small region of the nodes of the preceding layer.

In the displayed embodiment, the input layer 63 comprises 36 nodes 68, arranged as a two-dimensional 6×6 matrix. The convolutional layer 64 comprises 72 nodes 69, arranged as two two-dimensional 6×6 matrices, each of the two matrices being the result of a convolution of the values of the input layer with a kernel. Equivalently, the nodes 69 of the convolutional layer 64 can be interpreted as arranges as a three-dimensional 6×6×2 matrix, wherein the last dimension is the depth dimension.

A pooling layer 65 can be characterized by the structure and the weights of the incoming edges and the activation function of its nodes 70 forming a pooling operation based on a non-linear pooling function f. For example, in the two dimensional case the values $x^{(n)}$ of the nodes 70 of the pooling layer 65 can be calculated based on the values $x^{(n-1)}$ of the nodes 69 of the preceding layer 64 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 65 the number of nodes 69, 70 can be reduced, by replacing a number $d_1 \cdot d_2$ of neighboring nodes 69 in the preceding layer 64 with a single node 70 being calculated as a function of the values of said number of neighboring nodes in the pooling layer. In particular, the pooling function f can be the max-function, the average or the L2-Norm. In particular, for a pooling layer 65 the weights of the incoming edges are fixed and are not modified by training.

The advantage of using a pooling layer 65 is that the number of nodes 69, 70 and the number of parameters is reduced. This leads to the amount of computation in the network being reduced and to a control of overfitting.

In the displayed embodiment, the pooling layer 65 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 66 can be characterized by the fact that a majority, in particular, all edges between nodes 70 of the previous layer 65 and the nodes 71 of the fully-connected layer 66 are present, and wherein the weight of each of the edges can be adjusted individually.

In this embodiment, the nodes 70 of the preceding layer 65 of the fully-connected layer 66 are displayed both as two-dimensional matrices, and additionally as non-related nodes (indicated as a line of nodes, wherein the number of nodes was reduced for a better presentability). In this embodiment, the number of nodes 71 in the fully connected layer 66 is equal to the number of nodes 70 in the preceding layer 65. Alternatively, the number of nodes 70, 71 can differ.

Furthermore, in this embodiment the values of the nodes 72 of the output layer 67 are determined by applying the Softmax function onto the values of the nodes 71 of the preceding layer 66. By applying the Softmax function, the sum of the values of all nodes 72 of the output layer 67 is 1, and all values of all nodes 72 of the output layer 67 are real numbers between 0 and 1. In particular, if using the convolutional neural network 62 for categorizing input data, the values of the output layer can be interpreted as the probability of the input data falling into one of the different categories.

A convolutional neural network 200 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are f(x)=max(0,x), the tangent hyperbolics function or the sigmoid function.

In particular, convolutional neural networks 62 can be trained based on the backpropagation algorithm. For preventing overfitting, methods of regularization can be used, e.g. dropout of nodes 68-72, stochastic pooling, use of artificial data, weight decay based on the L1 or the L2 norm, or max norm constraints.

FIG. 9 shows an example of a providing system 83 which is configured to perform the previously discussed methods. The providing system 83 has a first interface 77 for receiving input data and a second interface 78 configured for providing output data. A computation unit 79 can e.g. be formed by a CPU or GPU or a different processing unit 80, e.g. an FPGA, ASIC, Microcontroller, etc., and a memory 81, that can especially store a computer program 82 implementing the discussed methods. The providing system 83, can e.g. be a computer.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for parametrizing a function for evaluating a medical image dataset concerning a region of interest, the method comprising:
   receiving a training dataset including multiple training medical image datasets;
   acquiring at least one representation type of the region of interest based on the training medical image datasets;
   generating a respective representation parametrization of the training medical image datasets for each of the at least one representation type;
   determining, using an optimization algorithm, at least one relevant representation type, of the at least one representation type, based on the respective representation parametrizations, in response to the at least one representation type including more than one representation type;
   determining, using the optimization algorithm, a processing algorithm based on at least one of the at least one relevant representation type or the respective representation parametrizations, the processing algorithm configured to determine at least one output parameter based on the respective representation parametrizations; and
   providing the at least one relevant representation type and the processing algorithm or processing parameters describing the processing algorithm, wherein the optimization algorithm is configured to optimize performance of the processing algorithm when the processing algorithm operates on a set of training representations generated based on at least a subset of the training medical image datasets using at least one respective representation parametrization of the respective representation parametrizations.

2. The computer-implemented method of claim 1, further comprising at least one of:
   determining algorithm parameters of the processing algorithm by the optimization algorithm; or
   determining the algorithm parameters by a further optimization algorithm, by optimizing the performance of the processing algorithm when the processing algorithm operates on the respective representation parametrizations, or a further set of representation parametrizations based on a further subset of the training medical image datasets and the at least one relevant representation type, by varying the algorithm parameters.

3. The computer-implemented method of claim 2, wherein the processing algorithm is a processing algorithm included in a search space including a plurality of processing algorithms, each processing algorithm of the plurality of processing algorithms including a neural network architecture,
   wherein the determining the processing algorithm includes searching for the neural architecture of the plurality of processing algorithms, and
   wherein free parameters of the neural network defined by the respective processing algorithm are defined by the algorithm parameters.

4. The computer-implemented method of claim 2,
   wherein the processing algorithm is a processing algorithm included in a search space including a plurality of processing algorithms, and
   at least one of
      wherein the plurality of processing algorithms in the search space define multiple convolutional neural networks that differ with respect to at least one of connections between layers or a type of operation performed by the respective layer, or
      wherein the plurality of processing algorithms in the search space define multiple neural networks that differ with respect to at least one of connections between nodes or an activation function used in at least one of the nodes.

5. The computer-implemented method of claim 2, wherein at least one of:
  the at least on representation type includes a slice of an image volume defined by the medical image dataset, and the determining the at least one relevant representation type includes determining at least one of which slice of the image volume is selected or an orientation of the slice, or
  the at least one representation type includes a projection image of an image volume of the multiple training medical image datasets, and the determining the at least one relevant representation type includes determining a direction of the projection.

6. The computer-implemented method of claim 1, wherein the processing algorithm is a processing algorithm included in a search space including a plurality of processing algorithms, each processing algorithm of the plurality of processing algorithms including a neural network architecture,
  wherein the determining the processing algorithm includes searching the neural architecture of the plurality of processing algorithms, and
  wherein free parameters of the neural network defined by the respective processing algorithm are defined by the algorithm parameters.

7. The computer-implemented method of claim 6, wherein the algorithm parameters include input weights of nodes of the neural network.

8. The computer-implemented method of claim 1,
  wherein the processing algorithm is a processing algorithm included in a search space including a plurality of processing algorithms, and
  at least one of
    wherein the plurality of processing algorithms in the search space define multiple convolutional neural networks that differ with respect to at least one of connections between layers or a type of operation performed by the respective layer, or
    wherein the plurality of processing algorithms in the search space define multiple neural networks that differ with respect to at least one of connections between nodes or an activation function used in at least one of the nodes.

9. The computer-implemented method of claim 1, wherein the at least one representation type includes at least two of:
  a projection image;
  a multiplanar reformatted representation;
  a curved planar reformation;
  an unfolded representations of the region of interest;
  a masked image;
  a representation generated using histogram equalization; or
  a normalization.

10. The computer-implemented method of claim 1, wherein at least one of:
  the at least one representation type includes a slice of an image volume defined by the medical image dataset, and the determining the at least one relevant representation type includes determining at least one of which slice of the image volume is selected or an orientation of the slice, or
  the at least one representation type includes a projection image of an image volume of the multiple training medical image datasets, and the determining the at least one relevant representation type includes determining a direction of the projection.

11. The computer-implemented method of claim 1, further comprising:
  receiving representation information including a set of representation parametrizations; and
  selecting, by the optimization algorithm, at least one of
    one of or a subgroup of the representation parametrizations, in a first alternative, as at least one representation parametrization of the at least one relevant representation type, or
    one of or a subgroup of the representation parametrizations, in a second alternative, as at least one approximate representation parametrization of the at least one relevant representation type based on the at least one approximate representation parametrization.

12. The computer-implemented method of claim 1, further comprising:
  receiving user input, by at least one user, defining the at least one representation type.

13. The computer-implemented method of claim 1, wherein the determining the at least one relevant representation type includes, for at least a selected representation parametrization of the respective representation parametrizations, determining a measure of relevance of the selected representation parametrization by comparing an optimum measure for performance achieved in the optimization algorithm when using the selected representation parametrization to generate training representations with an optimum measure for performance achieved when not using the selected representation parametrization to generate training representations.

14. The computer-implemented method of claim 1, further comprising:
  determining a measure of influence, for pixels or voxels or groups of neighboring pixels or voxels of the respective representation parametrizations of the at least one relevant representation type, based on at least one of the determined processing algorithm or the algorithm parameters.

15. A non-transitory computer-readable medium storing a computer program including instructions which, when the computer program is executed by a computer, cause the computer to carry out the computer-implemented method of claim 1.

16. The computer implemented method of claim 1, further comprising:
  determining the at least one output parameter based on the medical image set and the processing algorithm; and
  providing the at least one output parameter.

17. The computer implemented method of claim 1, further comprising:
  determining the at least one output parameter based on the medical image set, the at least one relevant representation type, and the processing algorithm; and
  providing the at least one output parameter.

18. A computer-implemented method for evaluating medical image data, comprising:
  receiving a medical image dataset concerning a region of interest as input data;
  applying a function trained by a machine learning algorithm to the medical image dataset to determine at least one output parameter, the function including a processing algorithm at least one of determined or parametrized by an optimization algorithm by
    acquiring at least one representation type of a region of interest based on a multiple training medical image datasets, generating a respective representation parametrization of the training medical image datasets for each of the at least one representation type, determining, using the optimization algorithm, at least one relevant representation type, of the at least one representation type, based on the respective representation parametrizations, in response to the at least one representation type including more than one representation type, and determining, using the optimization algorithm, the processing algorithm based on at least one of the at least one relevant representation type or the respective representation parametrizations; and providing the at least one output parameter as output data.

19. A non-transitory computer-readable medium storing a computer program including instructions which, when the computer program is executed by a computer, cause the computer to carry out the computer-implemented method of claim 11.

20. A providing system, comprising:
a first interface, configured to receive input data;
a second interface, configured to provide output data; and
at least one processor, configured to cause the providing system to
receive a training dataset including multiple training medical image datasets,
receive representation information including at least one representation type,
generate a respective representation parametrization of the training medical image datasets for each of the at least one representation type,
determine, using an optimization algorithm, at least one relevant representation type, of the at least one representation type, based on the respective representation parametrizations, in response to the at least one representation type including more than one representation type, and
determine, using the optimization algorithm, a processing algorithm based on at least one of the at least one relevant representation type or the respective representation parametrizations, the processing algorithm configured to determine at least one output parameter based on the respective representation parametrizations,
wherein the optimization algorithm is configured to optimize performance of the processing algorithm when the processing algorithm operates on a set of training representations generated based on at least a subset of the training medical image datasets using at least one respective representation parametrization of the respective representation.

* * * * *